US010521901B2

(12) United States Patent
Ikemoto et al.

(10) Patent No.: US 10,521,901 B2
(45) Date of Patent: Dec. 31, 2019

(54) IMAGE PROCESSING APPARATUS

(71) Applicant: HOYA CORPORATION, Tokyo (JP)

(72) Inventors: Yousuke Ikemoto, Tokyo (JP); Tadashi Minakuchi, Saitama (JP); Atsushi Komoro, Ibaraki (JP); Toshio Tachibana, Tokyo (JP); Noriko Ota, Saitama (JP)

(73) Assignee: HOYA CORPORATION, Tokyo (JP)

( * ) Notice: Subject to any disclaimer, the term of this patent is extended or adjusted under 35 U.S.C. 154(b) by 103 days.

(21) Appl. No.: 15/106,955

(22) PCT Filed: Feb. 23, 2016

(86) PCT No.: PCT/JP2016/055144
§ 371 (c)(1),
(2) Date: Jun. 21, 2016

(87) PCT Pub. No.: WO2016/136698
PCT Pub. Date: Sep. 1, 2016

(65) Prior Publication Data
US 2017/0098301 A1     Apr. 6, 2017

(30) Foreign Application Priority Data

Feb. 27, 2015   (JP) ................................. 2015-037539

(51) Int. Cl.
*G06K 9/00* (2006.01)
*G06T 7/00* (2017.01)
(Continued)

(52) U.S. Cl.
CPC .............. *G06T 7/0012* (2013.01); *A61B 1/04* (2013.01); *G06T 7/90* (2017.01); *G06T 2207/10004* (2013.01); *G06T 2207/30096* (2013.01)

(58) Field of Classification Search
CPC ......... G06T 2207/30096; G06T 7/0012; G06T 7/90
See application file for complete search history.

(56) References Cited

U.S. PATENT DOCUMENTS 5,016,173 A *   5/1991   Kenet ................... A61B 5/0059
                                                        382/128
7,079,675 B2 *  7/2006   Hamer ............... G06K 9/00127
                                                        128/922
(Continued)

FOREIGN PATENT DOCUMENTS

EP       2386999 A2    11/2011
JP       5302984       10/2013
(Continued)

OTHER PUBLICATIONS

International Preliminary Report on Patentability in PCT/JP2016/055144, with English language translation, dated Sep. 8, 2017.
(Continued)

*Primary Examiner* — Avinash Yentrapati
(74) *Attorney, Agent, or Firm* — Greenblum & Bernstein, P.L.C.

(57) ABSTRACT

An image processing apparatus has an image data obtaining means configured to obtain image data acquired by photographing biological tissue, a score calculating means configured to calculate a score representing severity degree of lesion of the biological tissue photographed in an image represented by the image data for each pixel based on the image data, a reliability evaluation means configured to evaluate reliability of the score based on the image data, and a score reliability calculating means configured to calculate score reliability which represents a ratio of pixels of which scores having predetermined reliability to all the pixels of the image data.

20 Claims, 13 Drawing Sheets

(51) Int. Cl.
*A61B 1/04* (2006.01)
*G06T 7/90* (2017.01)

(56) References Cited

U.S. PATENT DOCUMENTS

| | | | | |
|---|---|---|---|---|
| 7,602,943 B2* | 10/2009 | Fukui | ................ | H04N 1/387 |
| | | | | 382/103 |
| 8,913,807 B1* | 12/2014 | Horn | ................ | G06K 9/4652 |
| | | | | 382/128 |
| 9,430,833 B2 | 8/2016 | Ikemoto | | |
| 9,532,762 B2* | 1/2017 | Cho | ................ | A61B 6/502 |
| 9,786,050 B2* | 10/2017 | Bhargava | ................ | G06K 9/0014 |
| 2003/0215133 A1* | 11/2003 | Gindele | ................ | H04N 1/6027 |
| | | | | 382/167 |
| 2008/0175464 A1* | 7/2008 | Brett | ................ | G06T 7/0012 |
| | | | | 382/131 |
| 2008/0193020 A1* | 8/2008 | Sibiryakov | ................ | G06K 9/00248 |
| | | | | 382/209 |
| 2009/0073257 A1* | 3/2009 | Tanaka | ................ | G06T 7/0012 |
| | | | | 348/45 |
| 2009/0074271 A1 | 3/2009 | Nakamura et al. | | |
| 2009/0097725 A1* | 4/2009 | Krupnik | ................ | A61B 1/00096 |
| | | | | 382/128 |
| 2009/0123064 A1* | 5/2009 | Gibbs | ................ | G06K 9/00362 |
| | | | | 382/165 |
| 2010/0208047 A1* | 8/2010 | Kitamura | ................ | A61B 1/041 |
| | | | | 348/65 |
| 2010/0296715 A1* | 11/2010 | Kinosada | ................ | A61B 5/055 |
| | | | | 382/131 |
| 2012/0052063 A1* | 3/2012 | Bhargava | ................ | G06K 9/6277 |
| | | | | 424/133.1 |
| 2012/0087556 A1* | 4/2012 | Dai | ................ | G06K 9/0014 |
| | | | | 382/128 |
| 2012/0095331 A1* | 4/2012 | Ohashi | ................ | G06T 7/0014 |
| | | | | 600/425 |
| 2012/0179013 A1* | 7/2012 | Saito | ................ | A61B 1/0638 |
| | | | | 600/339 |
| 2013/0095519 A1* | 4/2013 | Backman | ................ | A61B 5/0066 |
| | | | | 435/34 |
| 2013/0223714 A1* | 8/2013 | Lipton | ................ | G06T 7/0012 |
| | | | | 382/131 |
| 2014/0112559 A1* | 4/2014 | Freeman | ................ | A61B 5/0059 |
| | | | | 382/128 |
| 2014/0193074 A1* | 7/2014 | Huang | ................ | G06K 9/4642 |
| | | | | 382/180 |
| 2014/0320620 A1* | 10/2014 | Ikemoto | ................ | A61B 1/00009 |
| | | | | 348/71 |
| 2015/0022210 A1* | 1/2015 | Yokosawa | ................ | G01R 33/56341 |
| | | | | 324/318 |
| 2015/0181185 A1* | 6/2015 | Ikemoto | ................ | A61B 1/0684 |
| | | | | 348/71 |
| 2015/0187070 A1* | 7/2015 | Cheng | ................ | G06T 7/11 |
| | | | | 382/128 |
| 2015/0193929 A1* | 7/2015 | Ikemoto | ................ | A61B 1/00009 |
| | | | | 382/128 |
| 2016/0027179 A1* | 1/2016 | Takama | ................ | G06T 7/33 |
| | | | | 382/128 |
| 2016/0335478 A1* | 11/2016 | Bredno | ................ | G06K 9/00147 |
| 2017/0098301 A1* | 4/2017 | Ikemoto | ................ | A61B 1/04 |
| 2017/0245820 A1* | 8/2017 | Sakuragi | ................ | A61B 34/10 |

FOREIGN PATENT DOCUMENTS

| | | |
|---|---|---|
| JP | 2014-18332 | 2/2014 |
| JP | 2014-213094 A | 11/2014 |
| WO | 2007/108280 A1 | 9/2007 |
| WO | 2007/119295 A1 | 10/2007 |
| WO | WO 2014/013777 A1 | 1/2014 |

OTHER PUBLICATIONS

U.S. Appl. No. 15/106,978 to Yousuke Ikemoto et al., which was filed on Jun. 21, 2016.
U.S. Appl. No. 15/106,968 to Yousuke Ikemoto et al., which was filed on Jun. 21, 2016.
Office Action issued in EPO family member Patent Appl. No. 16727926.4, dated Jul. 3, 2018.

* cited by examiner

IMAGE PROCESSING APPARATUS

TECHNICAL FIELD

The present invention relates to an image processing apparatus configured to process an image of a biological tissue.

BACKGROUND ART

There has been known an endoscope configured to analyze color information of an endoscopic image and obtain information (hereinafter, referred to as biological information) regarding condition of a biological tissue which is an object.

In Japanese Patent Publication No. 5302984 (hereinafter, referred to as patent document 1), an endoscope system configured to generate an oxygen saturation image which is imaged information regarding oxygen saturation degree of bloodstream hemoglobin is described. The endoscope system disclosed in patent document 1 is configured to obtain the oxygen saturation degree for each pixel based on relationship between color signals of two frames which are photographed subsequently by alternately using two kinds of illuminating light having different wavelength spectra (i.e., white light and oxygen saturation degree measurement light which is a narrow band), and generate the oxygen saturation degree image represented by a color difference signal related to the oxygen saturation degree (i.e., pseudo-color). Further, the endoscope system disclosed in patent document 1 is further configured to calculate reliability of the oxygen saturation degree for each pixel, and determine saturation of the pseudo-color based on the reliability.

SUMMARY OF THE INVENTION

According to the endoscope system disclosed in patent document 1, only the reliability of the biographic tissue is evaluated and displayed for each pixel, and an image processing suitable to the reliability of an entire image (i.e., quality of photographing condition) cannot be done.

The present invention is made in view of the above circumstances and an object thereof is to provide an image processing apparatus capable of executing image processing in accordance with the reliability of biological tissue for an entire image.

According to an embodiment of the invention, there is provided an image processing apparatus, which has an image data obtaining means configured to obtain image data acquired by photographing biological tissue, a score calculating means configured to calculate a score representing severity degree of lesion of the biological tissue photographed in an image represented by the image data for each pixel based on the image data, a reliability evaluation means configured to evaluate reliability of the score based on the image data, and a score reliability calculating means configured to calculate score reliability which represents a ratio of pixels of which scores having predetermined reliability to the number of all the pixels of the image data.

In the image processing apparatus described above, the reliability evaluating means may have a halation determining means configured to determine whether each pixel is in a halation state based on a pixel value, and the reliability evaluating means may be configured to exclude pixels determined to be in the halation state from the pixels of which scores having the predetermined reliability.

In the image processing apparatus described above, the reliability evaluating means may have a dark part determining means configured to determine whether a pixel is of a dark part based on a pixel value thereof, and the reliability evaluating means may be configured to exclude pixels determined to be of the dark part from the pixels of which scores having the predetermined reliability.

Since precision of color information of a pixel of which intensity is extremely high or extremely low is low, the reliability of the score is also low. By providing means for determining a part where halation is occurring or pixels at a dark part, and categorizing the pixels determined to be in the part where halation is occurring or in the dark part as pixels of which scores have poor reliability, it becomes possible to evaluate the reliability appropriately.

In the image processing apparatus described above, there may be further provided a color space converting means configured to convert the pixel values of the image data into pixel values of an HSI (hue-saturation-intensity) space, and the reliability evaluating means may be configured to evaluate the reliability of the scores based on intensity of each pixel output by the color space converting means.

In order to calculate the reliability of the score, intensity information is required. Therefore, with use of the image data expressed in the HSI space, calculation of the reliability of the score is facilitated.

In the image processing apparatus described above, the reliability evaluation means may have a saturation determining means configured to determine whether each pixel is a saturated pixel of which any one of color channels is saturated based on a pixel value thereof, and the reliability evaluation means may be configured to exclude pixels determined to be the saturated pixels from the pixels of which scores having the predetermined reliability.

According to the above configuration, the reliability of the score is evaluated based on saturation of the color channels, which has not conventionally been considered, it becomes possible to more precise and appropriate evaluation of the reliability.

In the image processing apparatus described above, the saturation determining means may have a saturated channel number counting means configured to count the number of saturated color channels based on the pixel values, and the saturation determining means may be configured to determine the pixels each having a predetermined or more number of saturated color channels as the saturated pixel.

In the image processing apparatus described above, there is further provided a marking means configured to apply marks indicating distribution of the scores on the image, and the marking means may be configured to change modes of the marks depending on the score reliability.

According to such a configuration, it becomes possible to display the score distribution suitable to display the score reliability.

In the image processing apparatus described above, the marking means may be configured to execute first color mapping to change pixel colors of a lesion part to a color corresponding to the score.

In the image processing apparatus described above, the marking means may be configured to exclude the image area in which pixels of which reliabilities are low are locally existing.

According to the above configuration, calculation amount required for the first color mapping can be reduced.

In the image processing apparatus described above, the marking means may be configured to apply the first color mapping with use of different colors for pixels of which scores have the predetermined reliability and pixels of which scored do not have the predetermined reliability.

According to the above configuration, it is possible to obtain a color map from which presence/absence of reliability and the score can be grasped intuitively.

In the image processing apparatus described above, the marking means may be configured to apply a first type simplified marking process in which a mark is applied on an area, of which score is equal to or greater than a predetermined value, in the image.

According to the above configuration, it becomes possible to obtain the marking with which presence/absence of reliability and/or distribution of the scores can be grasped easily, with small calculation amount.

In the image processing apparatus described above, the mark is a sign or a graphic symbol, and the marking means may be configured to change at least one of a size, a color and a type of the mark based on the score.

In the image processing apparatus described above, the first type simplified marking process may apply a single mark on a centroid of an area in which the score exhibits a predetermined value or more, or on a pixel of which score exhibits the maximum value.

In the image processing apparatus described above, the first type simplified marking process may apply multiple marks on an area in which the score exhibits a predetermined value or more.

In the image processing apparatus described above, the first type simplified marking process may apply multiple marks so as not to overlap with each other.

In the image processing apparatus described above, the first type simplified marking process may apply marks on the pixels of which score exhibits a predetermined value or more, each mark having a size corresponding to the value of the score on which the mark is applied.

In the image processing apparatus described above, the marking means may be configured to apply a second type simplified marking process in which a mark is applied such that the mark encircles an area of which score is relatively high in the image.

In the image processing apparatus described above, the mark may be a ring encircling the area in which the scores are high, or the mark may be a plurality of sings or graphic symbols arranged to encircle the area in which the scores are high.

In the image processing apparatus described above, there may be further provided a reliability displaying means configured to display an evaluation result of the reliability of the score.

In the image processing apparatus described above, the reliability displaying means may be configured to have a score reliability displaying means which is configured to display score reliability.

In the image processing apparatus described above, the reliability displaying means may be configured to have a dark part information displaying means configured to display information regarding the number of pixels in the dark part.

In the image processing apparatus described above, the reliability displaying means may be configured to have a halation information displaying means configured to display information regarding the number of pixels in which halation is occurring.

In the image processing apparatus described above, the reliability displaying means may be configured to have a saturation information displaying means configured to display information regarding the number of saturated color channels.

In the image processing apparatus described above, the saturation information displaying means may be configured to execute second color mapping to change the colors of pixels in accordance with the number of saturated color channels.

In the image processing apparatus described above, the saturation information displaying means may be configured to execute the second color mapping with use of colors different from colors used in the first color mapping.

In the image processing apparatus described above, the marking means may be configured to execute the first color mapping using chromatic colors, while the saturation information displaying means may be configured to execute the second color mapping with use of achromatic colors.

In the image processing apparatus described above, quality of a photographing condition may be determined in accordance with a color balance of the image.

In the image processing apparatus described above, the image may be photographed with use of a single-broadband illumination light.

According to the embodiment of the present invention, it becomes possible to execute an image processing in accordance with the reliability of the biological tissues.

EMBODIMENT FOR CARRYING OUT THE INVENTION

Figure 1:
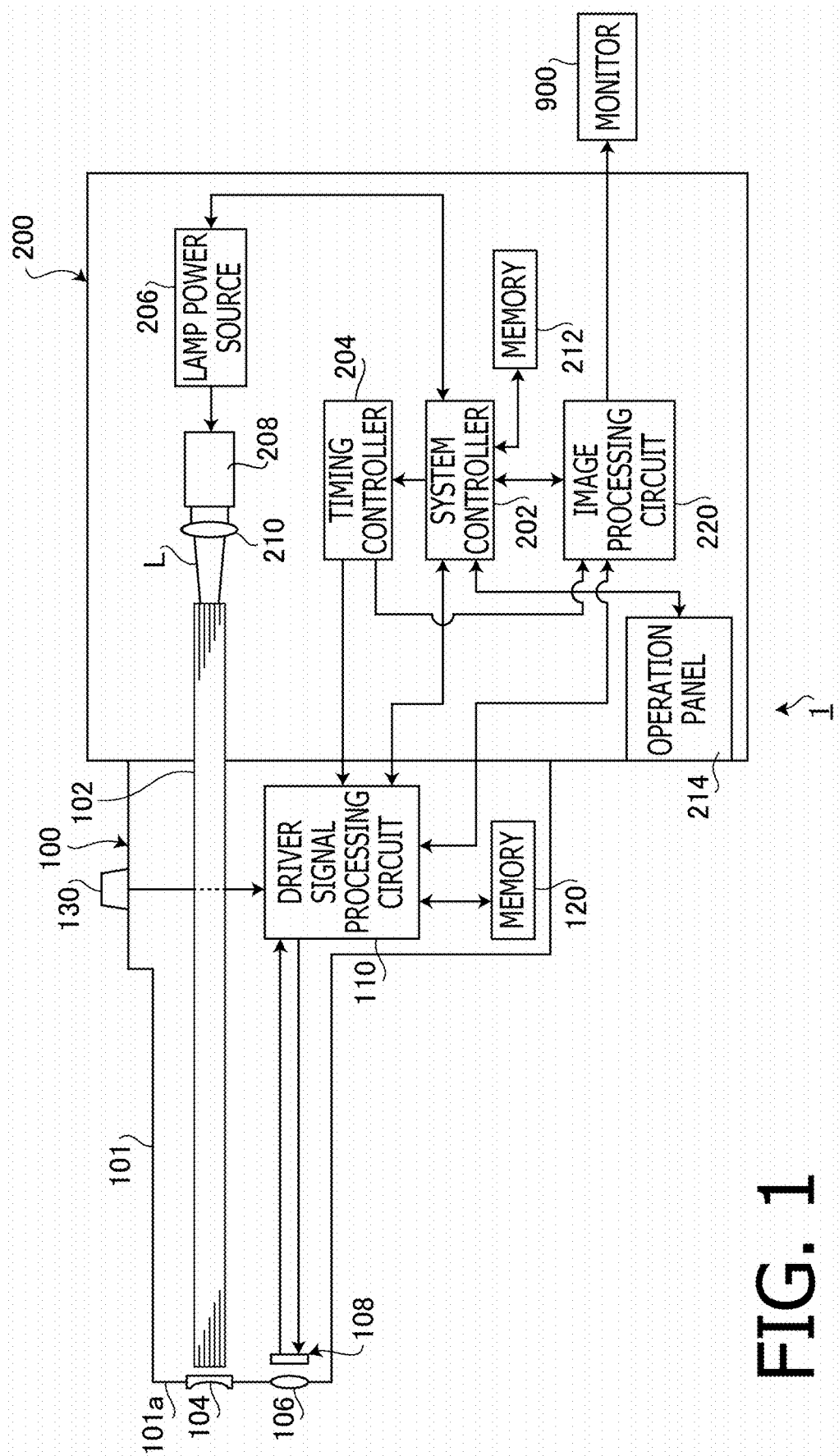
FIG. 1 is a block diagram schematically showing a configuration of an electronic endoscope apparatus according to an embodiment of the invention.

Hereinafter, referring to the drawings, embodiments of an image processing apparatus according to the present invention will be described. Incidentally, in the following description, an electronic endoscope system will be explained as one embodiment of the present invention.

[Entire Configuration of Electronic Endoscope Apparatus 1]

FIG. 1 is a block diagram showing a configuration of an electronic endoscope apparatus 1 according to the invention. As shown in FIG. 1, the electronic endoscope apparatus 1 is provided with an electronic scope 100, a processor 200 and a monitor 900.

The processor 200 is provided with a system controller 202 and a timing controller 204. The system controller 202 is configured to execute programs stored in a memory 212, and integrally control the electronic endoscope apparatus 1 entirely. The system controller 202 is connected to an operation panel 214. The system controller 202 changes operations of the electronic endoscope apparatus 1 and parameters for respective operations in accordance with instructions, which are input through the operation panel 214 by an operator. The timing controller 204 is configured to output synchronizing signals used to adjust operation timings of various parts to respective circuits of the electronic endoscope apparatus 1.

A lamp 208 is actuated by a lamp power source igniter 206, and then, irradiates illuminating light L. The lamp 208 is, for example, a high-intensity lamp such as a xenon lam, a halogen lamp, a mercury lamp and a metal halide lamp, or an LED (light emitting diode). The illuminating light L is broadband light having a spectrum ranging mainly from a visible light region to an invisible infrared region (or, white light including at least visible light region).

The illuminating light L irradiated by the lamp 208 is converged on an incident surface of an LCB (light carrying bundle) 102 by a converging lens 210, and enters into the LCB 102.

The illuminating light L entered the LCB 102 propagates inside the LCB 102, emitted from a light emitting surface of the LCB 102 which is arranged at a distal end of the electronic scope 100, and is incident on an object through a distribution lens 104. Return light from the object, which is illuminated by the illuminating light L, is converged, by an objective lens 106, to focus an optical image on a light receiving surface of a solid state imaging element 108.

The solid state imaging element 108 is a single CCD (charge coupled device) image sensor in accordance with a complementary color checkered color difference line sequential system). The solid state imaging element 108 picks up an optical image focused on the light receiving surface, and outputs an analog photographing signal. Specifically, the solid state imaging element 108 accumulates the optical image focused on respective pixels of the light receiving surface as electric charges corresponding to light amounts, generates yellow (Ye), cyan (Cy), green (G) and magenta (Mg) color signals, and sequentially outputs scan lines obtained by adding and mixing generated color signals of each two pixels arranged next to each other in a vertical direction. Incidentally, the solid state imaging element 108 needs not be limited to a CCD image sensor, but can be replaced with CMOS (complementary metal oxide semiconductor) image sensor, or any other type of imaging device. Further, the solid state imaging element 108 may be one mounting a primary color system filter (e.g., a Bayer array filter).

Inside a connection part of the electronic scope 100, a driver signal processing circuit 110 is provided. The analog photographing signal including the scan lines described above is input to the driver signal processing circuit 110 from the solid state imaging element 108 at a field period. Incidentally, in the following description, a term "field" could be replaced with a term "frame." In the embodiment, the field period and a frame period are ⅟60 second and ⅟30 second, respectively. The driver signal processing circuit 110 applies a predetermined processing to the analog photographing signal transmitted from the solid state imaging element 108, and outputs the same to an image processing circuit 220 of the processor 200.

The driver signal processing circuit 110 is also configured to access a memory 120 and retrieves intrinsic information which is intrinsic to the electronic scope 100. The intrinsic information of the electronic scope 100 recorded in the memory 120 includes, for example, the number of pixels, a sensitivity, an operable field rate, a model number of the solid state imaging element 108. The driver signal processing circuit 100 transmits the intrinsic information retrieved from the memory 120 to the system controller 202.

The system controller 202 executes various operations based on the intrinsic information of the electronic scope 100 to generates control signals. The system controller 202 controls operations and timings of circuits in the processor 200, with use of the generated control signals, so that processes suitable to the electronic scope connected to the processor 200 will be executed.

The timing controller 204 generates a synchronizing signal in accordance with a timing control by the system controller 202. The driver signal processing circuit 110 controls and drives the solid state imaging element 108, in accordance with the synchronizing signal supplied from the timing controller 204, at a timing synchronously with the field rate of a video signal generated by the processor 200.

The image processing circuit 220 generates image data based on the photographing signal output by the electronic scope 100, under control of the system controller 202. The image processing circuit 220 generates a screen data for monitor display using the generated image data, converts the screen data to a video signal having a predetermined video format, and outputs the same. The video signal is input to the monitor 900, and a color image of the object is displayed on a display screen of the monitor 900.

Figure 2:
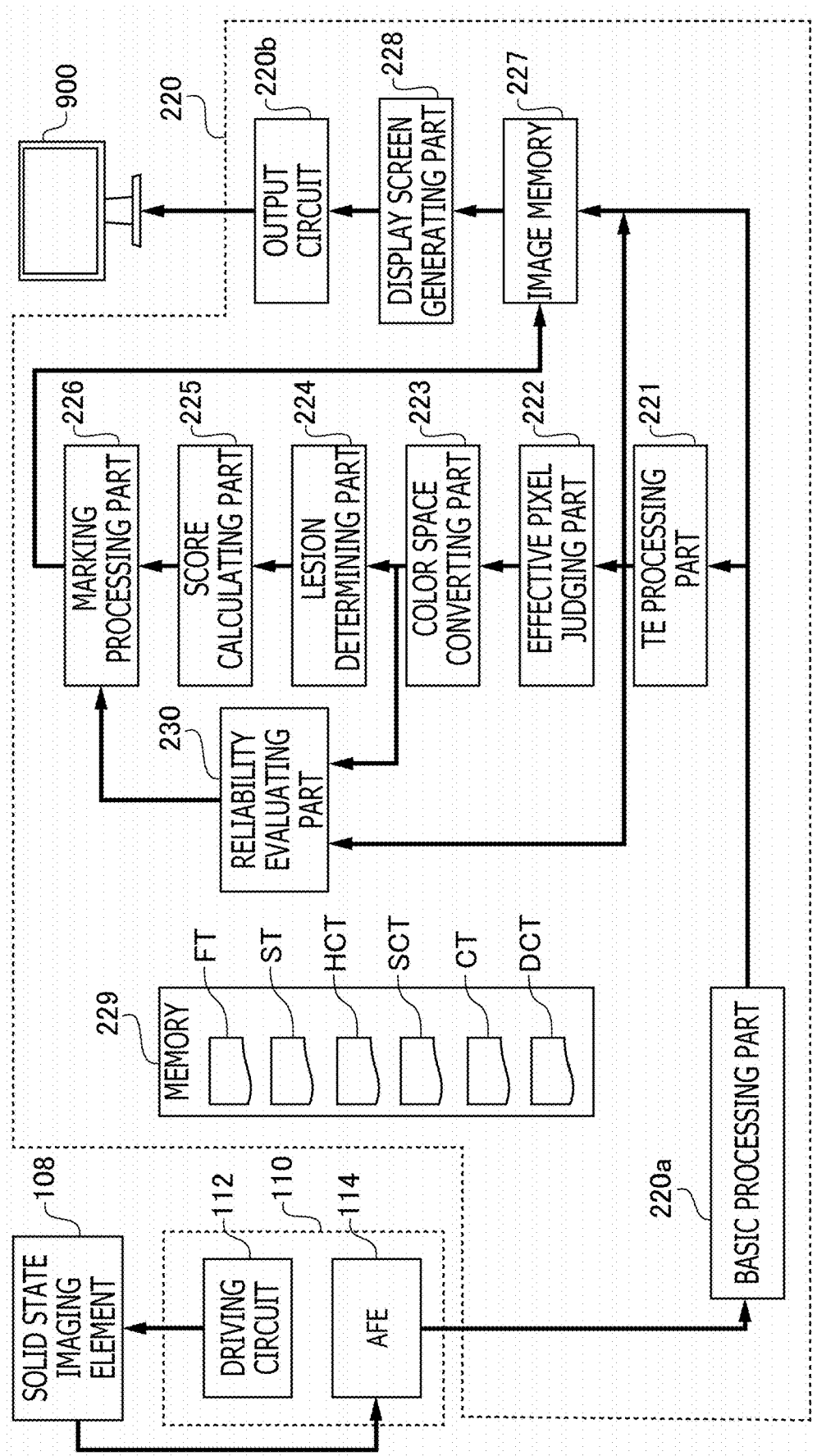
FIG. 2 is a block diagram schematically showing circuits regarding image processing of the electronic endoscope apparatus according to the embodiment of the invention.

FIG. 2 is a block diagram schematically showing a configuration of a circuit regarding image processing executed by the electronic endoscope apparatus 1.

The driver signal processing circuit 110 is provided with a driving circuit 112 and an AFE (analog front end) 114. The driving circuit 112 generates a driving signal of the solid state imaging element 108 in accordance with the synchronizing signal. The APE 114 applies noise reduction, signal amplification, gain compensation and A/D (analog to digital) conversion with respect to the analog photographing signal, and outputs a digital image signal, and outputs a digital photographing signal. Incidentally, all or a part of processing executed by the AFE 114 according to the embodiment may be executed by the solid state imaging element 108 or the image processing circuit 220.

The image processing circuit 220 is provided with a basic processing part 220a, an output circuit 220b, a TE (tone enhancement) processing part 221, an effective pixel judging part 222, a color space converting part 223, a lesion determining part 224, a score calculating part 225, a marking processing part 226, an image memory 227, a display screen generating part 228, a memory 229 and a reliability evaluating part 230. Processing executed by each part of the image processing circuit 220 will be described later.

Figure 3:
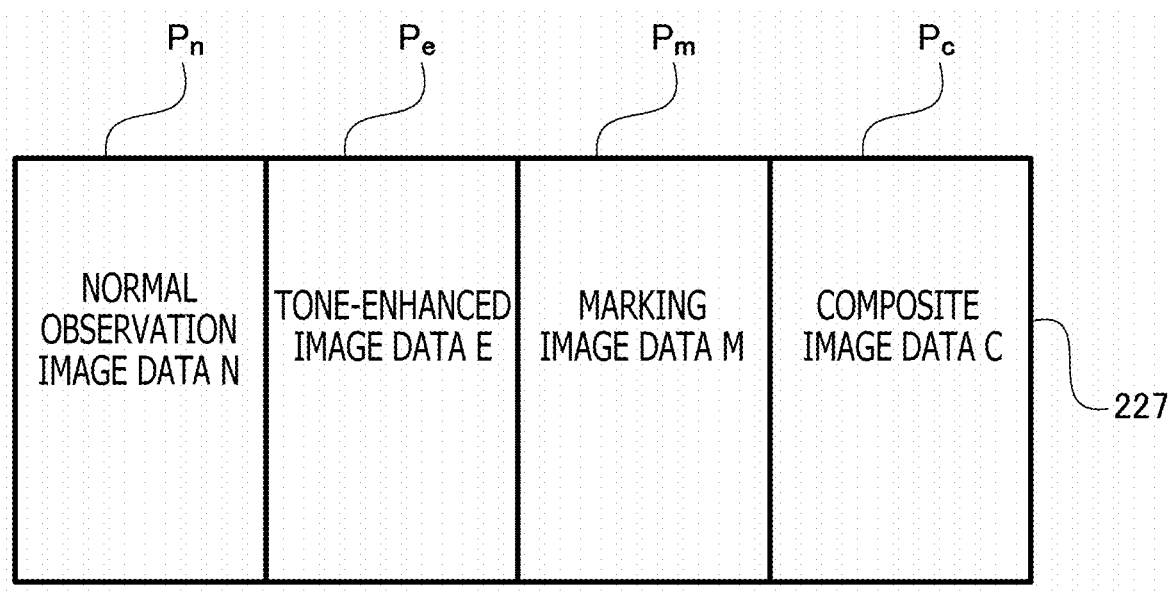
FIG. 3 is a drawing schematically showing a configuration of storage areas of an image memory.

FIG. 3 schematically shows a configuration of storage areas allocated in the image memory 227. In the image memory 227 according to the embodiment, four storage areas Pn, Pe, Pm and Pc are allocated. The storage area Pn is an area which stores normal observation image data N (i.e., image data representing a normal observation image NP) which is generated by the basic processing part 220a. Incidentally, in the storage area Pn, two pieces or more of normal observation image data N subsequently generated can be stored. Further, writing/retrieving of data in/from the storage area Pn is performed in accordance with a first-in first-out (FIFO) method. The storage area Pe is an area which stores TE image data E (i.e., image data representing TE image EP) generated by a TE processing part 221. The storage area Pm is an area which stores marking image data M (i.e., image data representing a marking image MP) generated by the marking processing part 226. The storage area $P_C$ is an area which stores composite image data C (i.e., image data representing a composite image CP) which is generated by composing the normal observation image data N (or the TE image data E) and the marking image data M.

As shown in FIG. 2, a flag table FT, a score table ST, a hue correlation value table HCT, a saturation correlation value table SCT, a reliability information table CT and a display color table DCT are stored in the memory 229. The flag table FT, and the score table ST are numeral value table having flags F (x, y) and scores Sc (s, y) representing analysis results regarding pixels (x, y) of the normal observation image data N, respectively. Specifically, the flags F (x, y) are parameters indicating presence/absence of lesions of tissues photographed on the corresponding pixels (x, y), the scores Sc (x, y) are parameters representing the severity degree of the lesions. The display color table DCT is a numerical value table defining a relationship between the scores Sc (x, y) and display colors (i.e., color codes) of the color map image (which is an aspect of the marking image MP), which will be described later. The hue correlation value table HCT and the saturation correlation value table SCT will be described later.

[Basic Processing S1]

Figure 4:
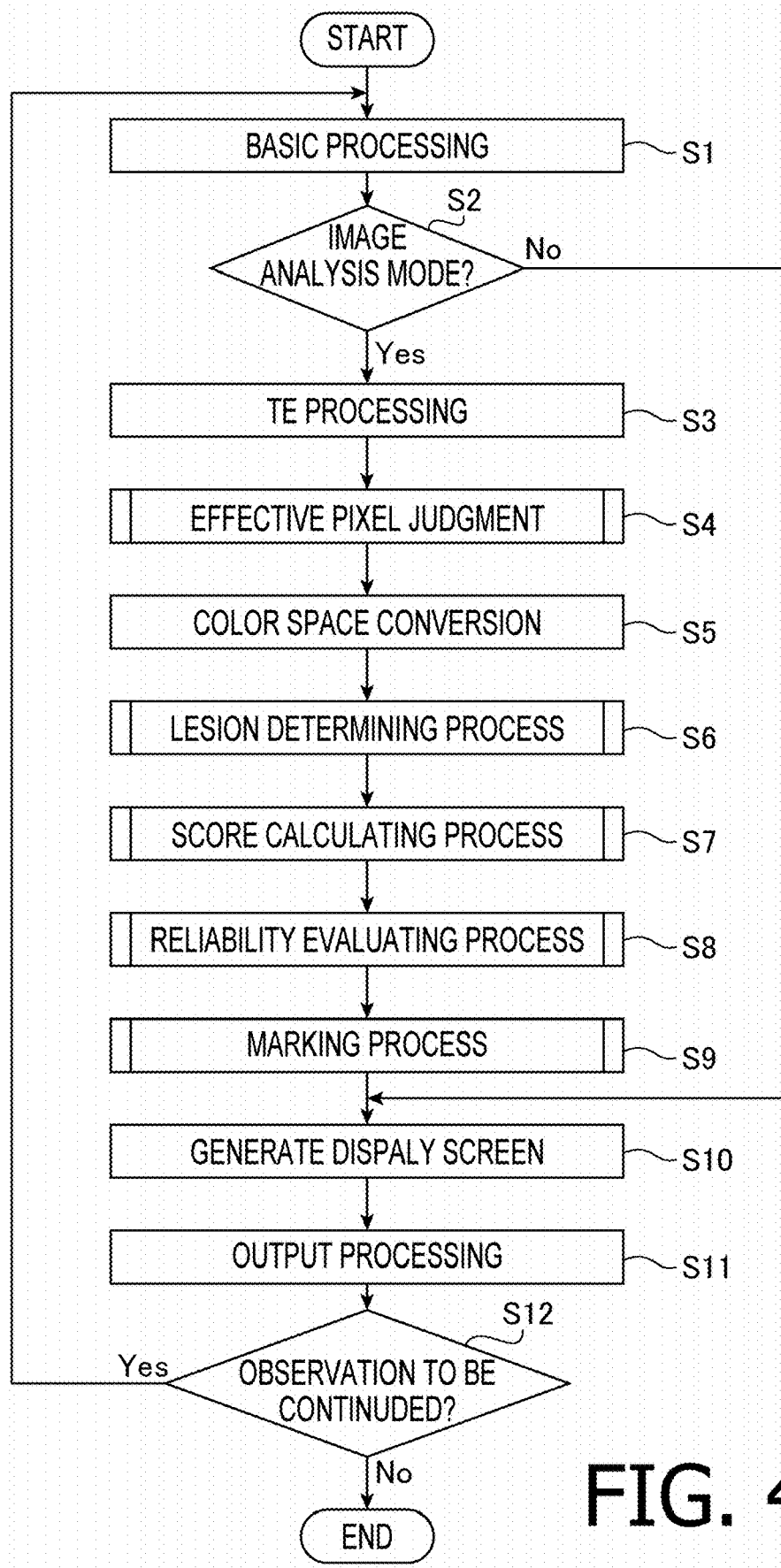
FIG. 4 is a flowchart illustrating a procedure of a process executed by an image processing circuit.

Next, processes executed by the image processing circuit 220 will be described. FIG. 4 is a flowchart illustrating procedures of the process executed by the image processing circuit 220. With respect to a digital signal output by the AFE 114, general signal processing (i.e., a basic processing S1) is applied by the basic processing part 220a, and normal observation image data N is generated.

The basic processing S1 includes a process of converting the digital photographing signal output by the AFE 114 to an intensity signal Y, and color difference signals Cb and Cr, a primary color separation process of separating primary colors R, G and B from the intensity signal Y, and color difference signals Cb and Cr, a clamp process of removing offset components, a defective pixel correction process of correcting a pixel value of a defective pixel with use of pixel values of surrounding pixels, a de-mosaic process (i.e., an interpolation process) of converting photographing data (i.e., RAW data) consisting of monochromatic pixel values to image data having full-color pixel values, a linear matrix process of correcting a spectral characteristic of the imaging element with use of a color matrix, a white balance process of compensating for spectral property of the illuminating light, and a contour correction process of compensating for deterioration of a spatial frequency characteristic.

Incidentally, all or part of the processes executed by the basic processing part 220a in the embodiment may be executed by the driver signal processing circuit 110 or the solid state imaging element 108.

The normal observation image data N generated by the basic processing part 220a is transmitted to the TE processing part 221 and the reliability evaluating part 230, and further stored in the storage area Pn of the image memory 227.

[Operation Mode Judging Process S2]

Next, whether an operation mode is set to an image analysis mode (S2) is judged. The image analysis mode according to the embodiment of the invention is an operation mode in which color information is analyzed with respect each pixel of the image data, it is judged whether each pixel is a pixel photographing a lesion part (hereinafter, referred to as a lesion pixel) based on the result of analysis of the color information and a predetermined judging criteria, and the lesion pixels are displayed in a discriminated manner. Kinds of lesions to be judged can be selected depending on inspection contents. In an example described below, pixels of color range which is intrinsic to observation images of inflammation (e.g., reddening inflammation including selling or easy bleeding) of inflammatory bowel disease (IBD) are displayed in a discriminated manner.

It is noted that the electronic endoscope apparatus 1 according to the embodiment is configured to operate in either of two operation modes: an image analysis mode; and a normal observation mode. The operation mode is switched by a user operation to an operation part 130 of the electronic scope 100 or the operation panel 214 of the processor 200. When the operation mode is set to the normal observation mode (S2: NO), process proceeds to S12.

[TE (Tone Enhancement) Process S3]

Figure 5:
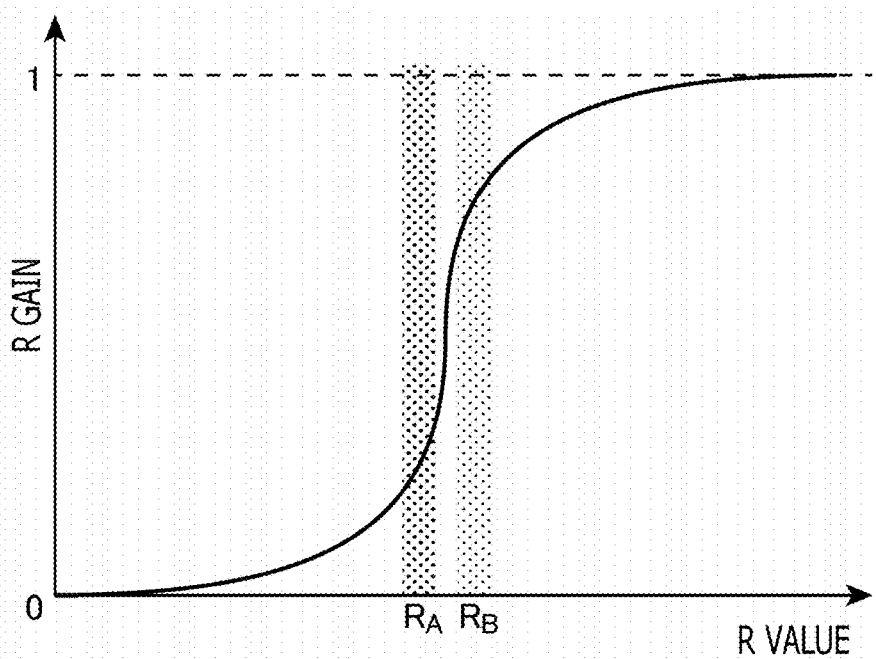
FIG. 5 shows an example of a gain curve used in a TE process.

When the image analysis mode is selected (S2: YES), the TE process S3, which is to be executed by the TE processing part 221, is executed subsequently. The TE process S3 is a process of increasing an effective resolution by performing gain adjustment to give a non-linear gain to each of primary color signals R, G and B of the normal observation image data N, thereby substantially expanding a dynamic range in the vicinity of a characteristic color range (in particular, a boundary portion thereof) of the lesion subject to judgment. Specifically, in the TE process S3, a process of applying the non-linear gain as shown in FIG. 5 to each of primary color signals R, G and B to obtain primary color signals R', G' and B' (i.e., TE image data E) is executed. For example, a gain curve shown in FIG. 5 is shaped such that an inclination of the curve is steep from a boundary range $R_A$, which is a characteristic color range of an ulcer, to a boundary region $R_B$, which is a characteristic color range of inflammation. By applying the gain in accordance with such a gain curve, a substantial dynamic range of the primary color signal R' (i.e., a signal obtained by applying the TE process S3 to the primary color signal R) from the boundary range $R_A$ to the boundary range $R_B$ can be expanded, thereby further precise threshold value judgment being enabled.

Incidentally, by the TE process S3, the hue changes such that the inflammatory part becomes reddish, the ulcer part becomes whitish and the normal part becomes greenish. Therefore, when the TE image data E, which is generated in the TE process S3, is displayed on the monitor 900, lesion part (e.g., the inflammatory part or the ulcer part) can easily be visually recognized in comparison with a case where the normal observation image data N before the TE process S3 is applied is displayed. It is noted that the TE process S3 above is an example of a color enhancement process applicable to the present invention. Instead of the TE process S3, another type of color enhancement process capable of enhancing color quality, specifically, the hue or contrast of saturation (or chromaticity), may be employed.

[Effective Pixel Judging Process S4]

After the TE process S3 has completed, the effective pixel judging part 222 applies the effective pixel judging process S4 to the TE image data E. It is noted that, the TE process S3 is omitted and the effective pixel judging process S4 may be applied to the normal observation image data N.

Figure 6:
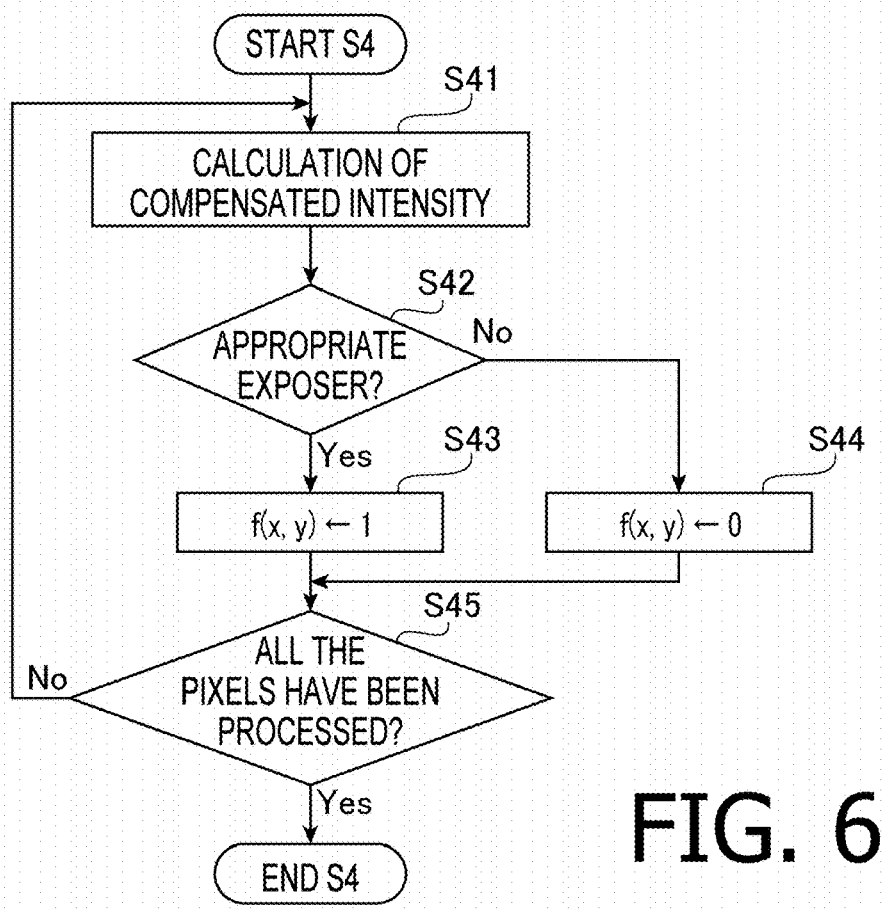
FIG. 6 is a flowchart illustrating a procedure of an effective pixel judging process.

FIG. 6 is a flowchart illustrating a procedure of the effective pixel judging process S4. The effective pixel judging process S4 is a process of judging whether pixel values are suitable for image analysis, and is sequentially executed to all the pixels (x, y) constituting the image data. In the effective pixel judging process S4, firstly, for each pixel (x, y), based on the primary color signals R'(x, y), G'(x, y), and B'(x, y) of the TE image data E, corrected intensity int(x, y) is calculated with use of formula 1 below.

$$\text{int}(x,y)=0.3*R'(x,y)+0.59*G'(x,y)+0.11*B'(x,y) \quad \text{[Formula 1]}$$

Incidentally, values of the corrected intensity int(x, y) as calculated are used in a following appropriate exposure judging process S42. Further, as known from formula 1, the corrected intensity int(x, y) is not a simple average of the primary color signals R'(x, y), G'(x, y) and B'(x, y), but is obtained as a weighted average based on relative spectral sensitivity characteristic of human beings (e.g., the operator).

Next, for each pixel (x, y), the appropriate exposure judging process S42 is executed, in which whether the exposure level is appropriate to image analysis is judged based on the corrected intensity int(x, y) of the TE image data E calculated in process S41 and the primary color signals R'(x, y), G'(x, y) and B'(x, y). In the appropriate exposure judging process S42, the exposure is determined to be the appropriate exposure (S42: YES) when at least one of (or both of) the following two conditions (i.e., formulae 2 and 3) is satisfied. Incidentally, formula 2 defines an upper limit value of the corrected intensity int(x, y) (the entire light amount), while formula 3 defines a lower limit value of each of the primary color signals R'(x, y), G'(x, y) and B'(x, y).

$$\text{int}(x,y)<235 \quad \text{[Formula 2]}$$

$$\text{Max}\{R'(x,y),G'(x,y),B'(x,y)\}>20 \quad \text{[Formula 3]}$$

If, for the pixel (x, y), it is determined that formula 2 or formula 3 (or both formulae 2 and 3) is satisfied and the exposure is appropriate (S42: YES), the effective pixel judging part 222 rewrites the value of a flag F(x, y), which corresponds to the pixel (x, y), of the flag table FT stored in the memory 229 with value "1" (S43).

It is noted that the flag F (x, y) has a flag value of one of 0-2. Each flag value is defined below.

0: invalid pixel data
1: normal or unjudged (pixel data is valid)
2: lesion (inflammation)

In the appropriate exposure judging process S42, if none of the formulae 2 and 3 is satisfied (or one of the formulae 2 and 3 is not satisfied), and the exposure is determined to be inappropriate (S42: NO), the effective pixel judging part 222 rewrites the value of the flag F(x, y) with "0" (S44).

In process S45, it is judged whether the process has been completed for all the pixels (x, y). Unless all the pixels (x, y) have been processed, the above processes S41-S45 are repeated.

[Color Space Converting Process S5]

When the effective pixel judging process S4 has completed, the color space converting part 223 applies a color space converting process S5 to the TE image data E. The color space converting process S5 is a process of converting pixel values of an RGB space defined by RGB three primary colors to pixel values of HIS (Hue-Saturation-Intensity) space defined by three elements of hue, saturation and intensity. Specifically, in the color space converting process S5, the primary color signals R'(x, y), G'(x, y) and B'(x, y) of each pixel (x, y) of the TE image data E is converted to hue H(x, y), saturation S(x, y) and intensity I(s, y).

Further, data of under or over exposure pixels (x, y) has low accuracy and lowers reliability of the analysis results. Therefore, the color space converting process S5 is applied only to the pixels (x, y) of which the value of the flag F(x, y) is set to be one (1) (i.e., the pixels (x, y) judged to be appropriately exposed in the effective pixel judging process S4).

Decision image data J{H(x, y), S(x, y), I(x, y)} having hue H(x, y), saturation S(x, y) and intensity I(x, y) of each pixel (x, y), which are generated by the color space converting part 223, is transmitted to the lesion determining part 224.

[Lesion Determining Process S6]

After completion of the color space conversion process S5, the lesion determining part 224 executes a lesion judging process S6 using the decision image data J. the lesion determining process S6 is a process applied to each pixel (x, y) of the endoscope image, in which process a condition of the biological tissue photographed by the pixel is determined (i.e., it is judged whether the biological tissue is in the inflammatory condition) depending on whether the decision image data J is plotted on which of areas α or β (see FIG. 8; described later) in an HS space (i.e., Hue-Saturation space). It is noted that the HS space is, similar to the a chromaticity space, a space representing quality of colors (i.e., components excluding brightness/intensity). For example, when the image analysis is performed on another color space such as a CIE 1976 L*a*b* color space, lesion determination by the lesion determining part 224 is executed on the chromaticity space (e.g., an a*b*space).

Figure 7:
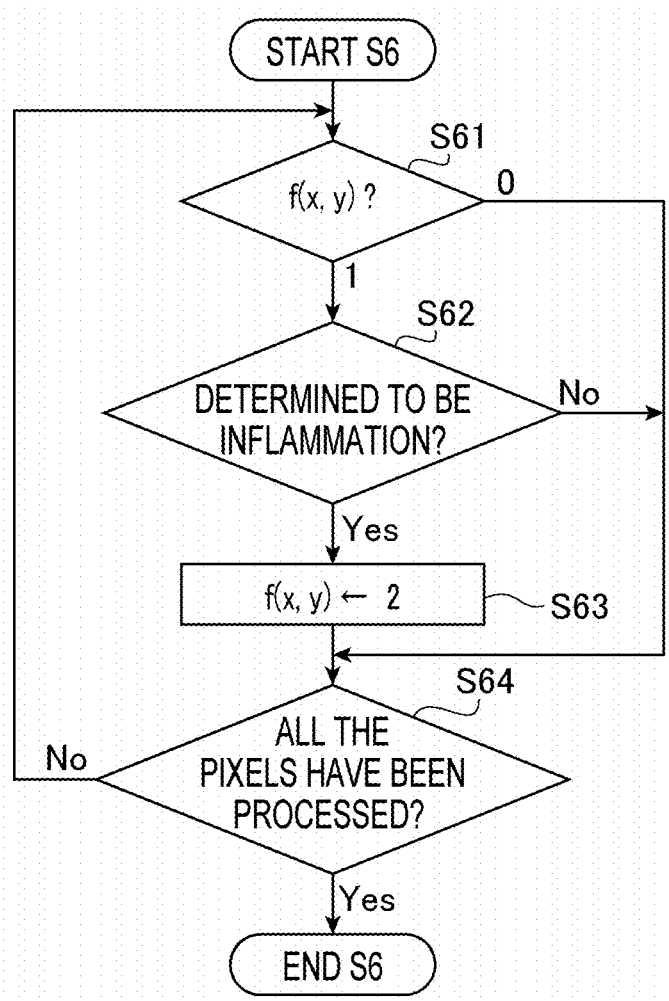
FIG. 7 is a flowchart illustrating a procedure of a lesion judging process.

FIG. 7 is a flowchart illustrating a procedure of the lesion determining process S6. The lesion determining process S6 is executed for all the pixels (x, y) constituting the image data, sequentially. In the lesion determining process S6, firstly, it is determined whether data of each pixel (x, y) is valid, referring to the flag table FT (S61). When the value of the flag F(x, y) is "1" (i.e., the pixel data is valid), an inflammation determining process S62 is executed. When the value of the flag F(x, y) is "0" (i.e., the pixel data is invalid), control proceeds to process S64 without executing the inflammation determining process S62.

Figure 8:
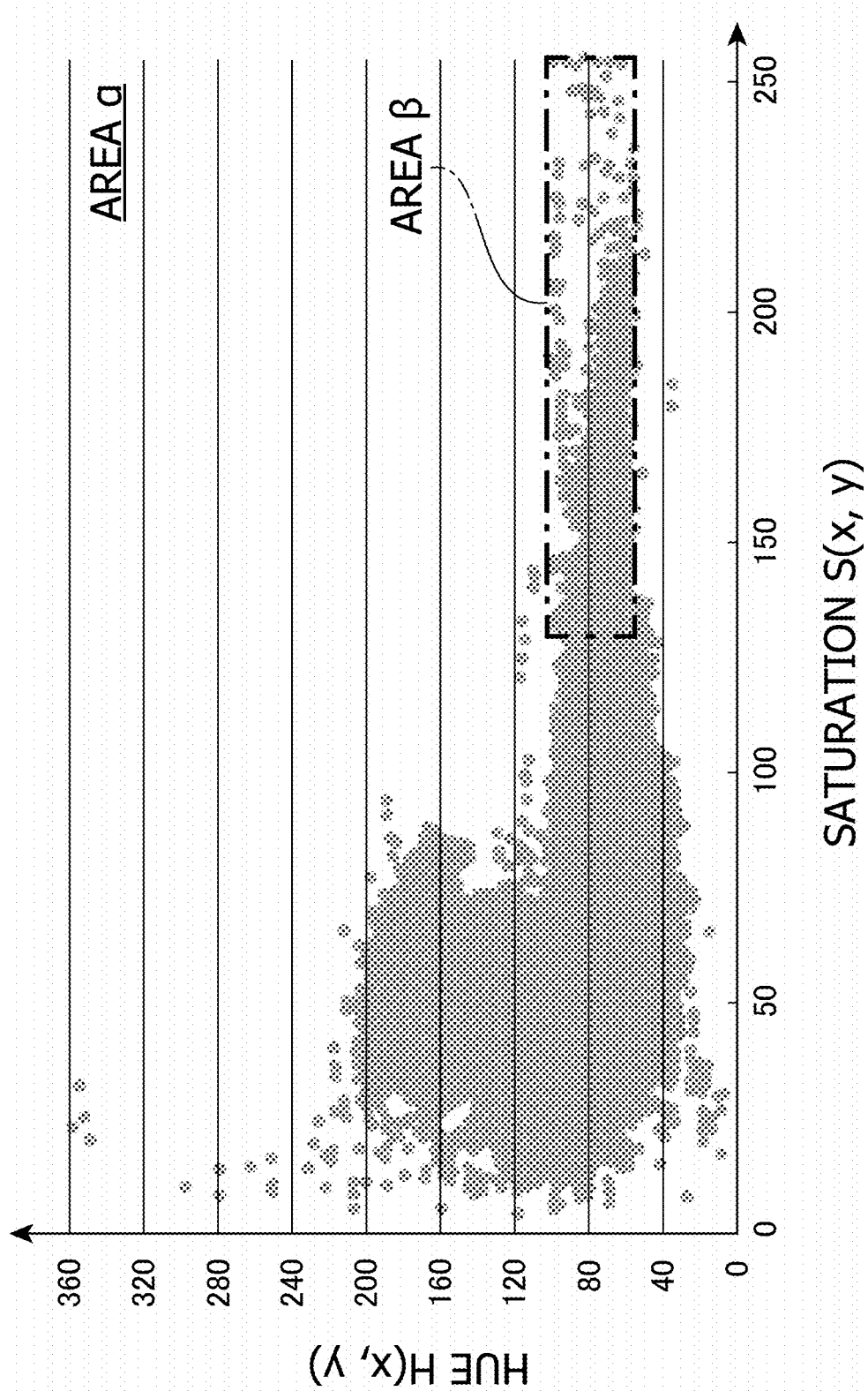
FIG. 8 is a scatter diagram in which pixel values of biological tissues are plotted in an HS coordinate space.

The inflammation determining process S62 will be described. FIG. 8 is a scatter diagram which shows that decision image data J obtained from the endoscope image data of a plurality of inflammatory bowel disease patients is plotted in an HS coordinate space.

The scatter diagram shown in FIG. 8 is classified into area β which is located on a lower right portion and encircled by broken lines, and area a which is an area other than area β. According to the research of the inventors of the present invention, it has become clear that most of the portions determined as inflammatory portions by doctors who are skilled in endoscopic diagnosis of the inflammatory bowel disease are plotted in area β, while most of the portions determined as non-inflammatory portions by the doctors skilled in endoscopic diagnosis of the inflammatory bowel disease are plotted in area α. From the above, the condition of the biological tissue (i.e., presence/absence of the inflammation) can be judged with sufficient accuracy based on the two pieces of information of the hue (shade of color) and saturation (vividness of color) of the endoscopic observation image photographing biological tissues.

In the inflammation determining process S62, it is determined whether decision image data J{H(x, y), S(x, y)} of each pixel (x, y) is to be plotted in area β shown in FIG. 8. Specifically, the decision image data J{H(x, y), S(x, y)} is plotted in area β when both formulae 4 and 5 below are satisfied. When the decision image data J{H(x, y), S(x, y)} does not satisfy at least one of formulae 4 and 5, the decision image data J{H(x, y), S(x, y)} is plotted in area α (i.e., it is determined that the pixels are not those of the inflammatory portions). Incidentally, $\delta_{S1}$, $\delta_{H1}$ and $\delta_{H2}$ are compensation values which can be set by the operator, and by the settings of these compensation values, strictness of decision (i.e., sensitivity) can be appropriately adjusted.

$$130+\delta_{S1} \leq S(x,y) \qquad \text{[Formula 4]}$$

$$60+\delta_{H1} \leq H(x,y) \leq 100+\delta_{H2} \qquad \text{[Formula 5]}$$

When the decision image data J{H(x, y), S(x, y)} of a pixel (x, y) is plotted in area β (S62: YES): the value of the flag F(x, y) corresponding to the pixel (x, y) is rewritten with "2" (i.e., inflammation) (S63), and control proceeds to process S64. When the decision image data J{H(x, y), S(x, y)} of a pixel (x, y) is not plotted in area β (S62: NO), the flag F(x, y) is not rewritten, and control proceeds to process S64.

In process S64, it is judged whether all the pixels (x, y) have been processed. Until all the pixels (x, y) are processed, above processes S61-S64 are repeated.

[Score Calculating Process S7]

After the lesion determining process S6 has completed, a score calculating process S7 is executed. The score calculating process S7 is a process of calculating a score Sc(x, y) representing an evaluation value of severity degree of the lesion part based on the pixel values of the decision image data J. The score calculating process S7 is executed sequentially for all the pixels (x, y). Incidentally, an algorithm of the score calculation explained below is only an example, and the present invention can be applied to displayed screens of scores calculated in various algorithms, respectively.

[Principle of Score Calculation]

Here, a principle of score calculation according to the embodiment will be described briefly. It is known that the more a symptom of an inflammatory part progresses, the closer the color of the inflammatory part becomes the color of blood as superficial normal mucous membranes will be fallen out. Therefore, degree of correlation between the color of the inflammatory part and the color of the blood (i.e., correlation value CV, which will be described later) serves as a good index representing the severity degree of the inflammatory part. According to the present embodiment, the correlation value CV(x, y) representing the relative correlation between the decision image data J{H(x, y), S(x, y)} of each pixel (x, y) and a color of the blood (i.e., hue and saturation) is calculated, which is used as the score Sc(x, y) representing the severity of the inflammatory part.

[Lesion Part Judgment S71]

Figure 9:
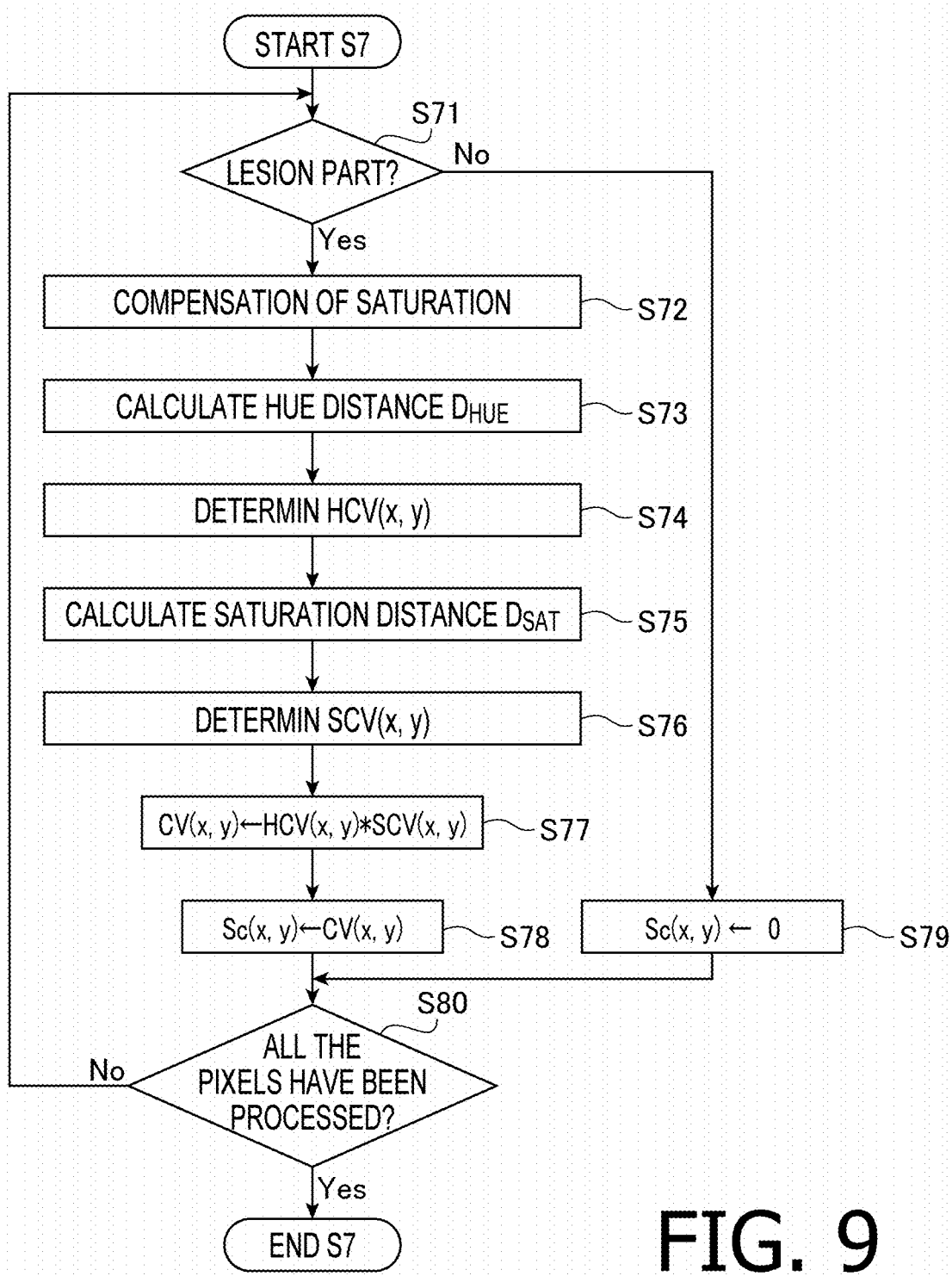
FIG. 9 is a flowchart illustrating a procedure of a score calculating process.

FIG. 9 is a flowchart illustrating a procedure of the score calculation process S7. In the score calculation process S7, the flag table FT is firstly retrieved, and it is judged whether the value of the flag F(x, y) corresponding to the pixel (x, y) is "2" (i.e., inflammation) (S71).

When the value of the flag F(x, y) is "2" (inflammation), namely, when the pixel (x, y) is the lesion pixel (S71: YES), process proceeds to S72. When the pixel (x, y) is not the lesion pixel (S71: NO), process proceeds to S79.

[Compensation of Saturation: S72]

It is known that saturation of blood or biological tissue including blood depends on its intensity. Specifically, saturation thereof is lower as the intensity is higher. In S72, variation of saturation S(x, y) due to intensity I(x, y) of the decision image data J(x, y) is compensated using formula 6 which is developed by the present inventors. By applying this compensation, it is possible to make precision of score calculation higher.

$$\begin{bmatrix} I_{corr.}(x, y) \\ S_{corr.}(x, y) \end{bmatrix} = \begin{bmatrix} \cos\theta & -\sin\theta \\ \sin\theta & \cos\theta \end{bmatrix} \begin{bmatrix} I(x, y) \\ S(x, y) \end{bmatrix} + \begin{bmatrix} I_{ref} \\ S_{ref} \end{bmatrix} \qquad \text{[Formula 6]}$$

where,

Icorr.(x, y): intensity of the decision image data J after compensation;

Scorr.(x, y): saturation of the decision image data J after compensation;

Iref.: intensity of blood sample data serving as a reference value; and

θ: an angle providing with a correlation index (cos θ) between the saturation and the intensity of the blood sample. It is noted that the correlation index (measured value) is −0.86, and accordingly, θ=149.32 (degree) is used.

[Calculation of Hue Distance $D_{HUE}$: S73]

Next, using formula 7, a hue distance $D_{HUE}$(x, y) is calculated (S73). The hue distance $D_{HUE}$ is a relative value of the hue of the decision image data J(x, y) using the hue $H_{ref}$ of the blood sample data as reference.

$$D_{HUE}(x,y) = H(x,y) - H_{ref} \qquad \text{[Formula 7]}$$

[Determination of Hue Correlation Value HVC: S74]

Figure 10:
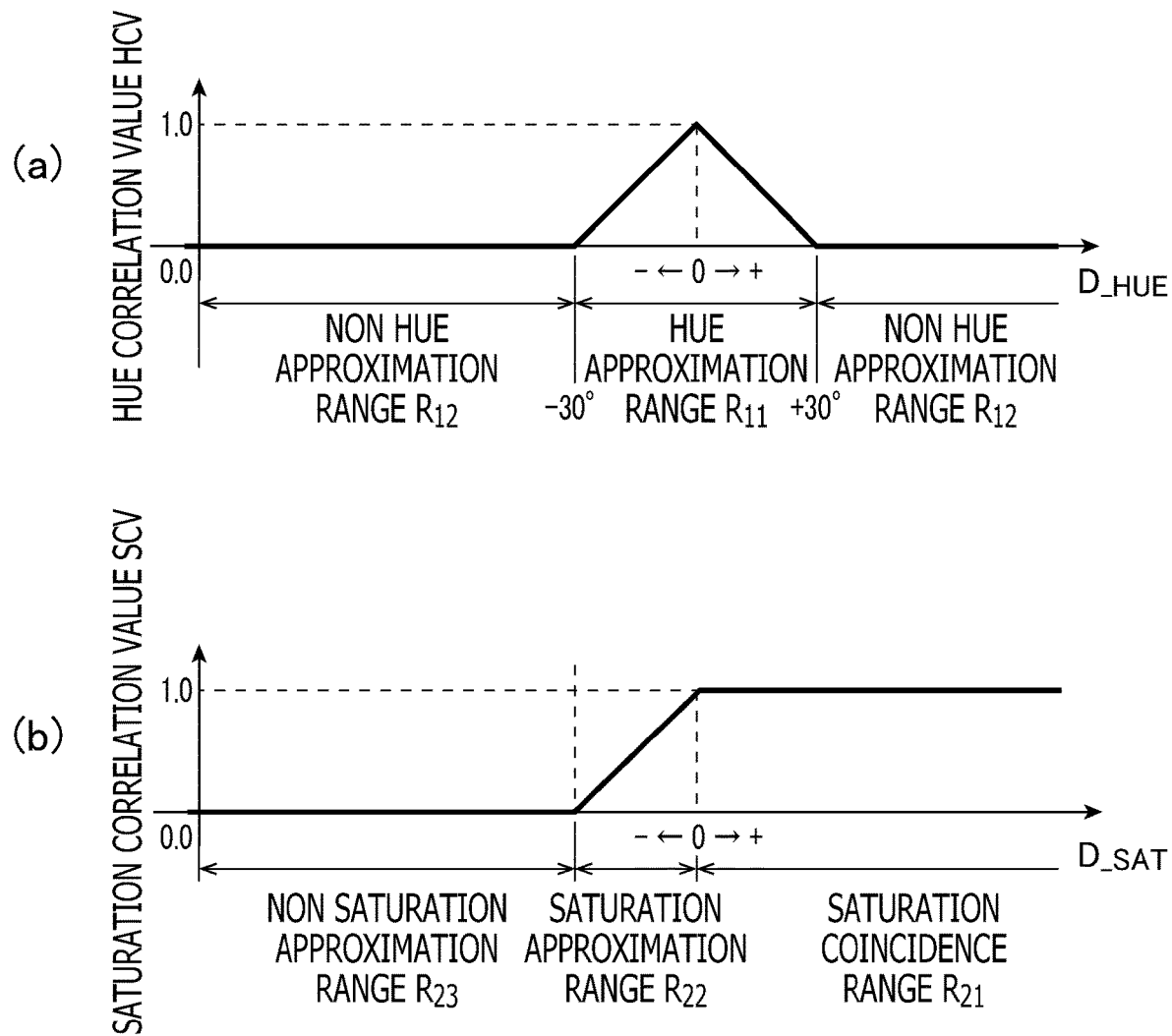
FIG. 10 shows graphs showing relationships between a hue distance, a saturation distance and correlation values.

Next, a hue correlation value HVC(x, y) is determined (S74) based on the hue distance $D_{HUE}$(x, y). The hue correlation value HCV(x, y) is a parameter having strong correlation with severity degree of an inflammation part. FIG. 10(a) is a graph showing a relationship between the hue distance $D_{HUE}$ and the hue correlation value HCV. The hue distance $D_{HUE}$ exhibits a strong correlation with the severity degree of the inflammation part within a range of ±30° (hereinafter, referred to as a "hue approximation range $R_{11}$"), while exhibits little correlation in other ranges. Therefore, the hue correlation value HCV(x, y) of the present embodiment is set to a minimum value of 0.0 in a non-hue approximation range $R_{12}$, and set to linearly increase as the hue distance $D_{HUE}$(x, y) approaches 0° within the hue approximation ranges $R_{11}$. Further, the hue correlation value HCV(x, y) is normalized such that the minimum and maximum values of the hue correlation values HCV(x, y) are 0.0 and 1.0, respectively.

The relationship between the hue distance $D_{HUE}$ and the hue correlation value HCV shown in FIG. 10(a) is stored in the memory 229 in form of a hue correlation value table HCT. By referring to the hue correlation value table HCT, a hue correlation value HCV(x, y) corresponding to a hue distance $D_{HUE}$(x, y) can be obtained.

[Calculation of Saturation Distance: S75]

Next, a saturation distance $D_{SAT}$(x, y) is calculated using formula 8. The saturation distance $D_{SAT}$(x, y) is a relative value of saturation of the decision image data J(x, y) using saturation $S_{ref}$ of the blood sample data as reference.

$$D_{SAT}(x,y) = S_{curr}(x,y) - S_{ref} \qquad \text{[Formula 8]}$$

[Determination of Saturation Correlation Value SCV: S76]

Next, a saturation correlation value SCV(x, y) is determined based on the saturation distance $D_{SAT}(x, y)$ (S76). The saturation correlation value SCV(x, y) is also a parameter having strong correlation with the severity degree of the inflammation part. FIG. 10(b) is a graph showing a relationship between the saturation distance $D_{SAT}(x, y)$ and the saturation correlation value SCV. The saturation distance $D_{SAT}(x, y)$ has strong correlation with the severity degree of the inflammation part in a negative range in which the saturation distance $D_{SAT}$ has a value equal to or greater than a predetermined value (hereinafter, referred to as a saturation approximation range $R_{22}$), while the saturation distance $D_{SAT}$ has little correlation in a negative range and the saturation distance $D_{SAT}$ has a value equal to or less than the predetermined value. Further, in a range in which the saturation distance $D_{SAT}$ is zero or greater, that is, in a range where the saturation of the lesion pixel is equal to or greater than the saturation Sref of the blood sample data (hereinafter, referred to as saturation coincidence range $R_{21}$), it is considered that the severity degree is quite high. Therefore, the saturation correlation value SCV(x, y) according to the present embodiment is configured such that the saturation correlation value SDV(x, y) is set to have the maximum value of 1.0 within the saturation coincidence range $R_{21}$, set to have the minimum value of 0.0 within the non-saturation approximation range $R_{23}$, and set to linearly increase within the saturation approximation range $R_{22}$. It is noted that the saturation correlation value SCV(x, y) is also a normalized value which has the minimum value of 0.0 and the maximum value of 1.0.

The relationship between the saturation distance $D_{SAT}$ and the saturation correlation value shown in FIG. 10(b) is stored in the memory 229 in form of a saturation correlation value table SCT. By referring to the saturation correlation table SCT, a saturation correlation value SCV(x, y) corresponding to a saturation distance $D_{SAT}(x, y)$ can be obtained.

[Calculation of Correlation Value: S77]

Next, by multiplying the hue correlation value HCV(x, y) with the saturation correlation value SCV(x, y), a correlation value CV(x, y) between the color of a lesion pixel (x, y) and the color of blood. It is noted that the correlation value CV(x, y) is a normalized value of which the minimum value is 0.0 and the maximum value is 1.0. Further, the correlation value CV(x, y) is divided into eleven steps with a pitch of 0.1 point.

[Update of Score Sc: S78]

Since the correlation value CV(x, y) serves as an appropriate index of severity degree of the inflammation, the value of the score Sc(x, y) in the score table ST is rewritten with the correlation value CV(x, y) (S78).

[Updating of Score Sc: S79]

When a pixel (x, y) is not the lesion pixel (S71: NO), the above-described calculation of the correlation value CV(x, y) is not executed, and the value of the score Sc(x, y) in the score table ST is rewritten with "0" (S79). According to this configuration, scores Sc(x, y) can be given to all the pixels (x, y) with a smaller amount of calculations.

In process S80, it is judged whether the processing has been completed for all the pixels (x, y). Until processing has been completed for all the pixels (x, y), above-described processes S71-S80 are repeated.

[Reliability Evaluation: S8]

After the score calculating process S7, a reliability evaluating process S8 by the reliability evaluating part 230 is executed.

Now, general description of the reliability evaluating process S8 according to the present embodiment will be made. As described above, the score Sc(x, y) is calculated based on the color information of the TE image EP. Therefore, accuracy of the score Sc(x, y) depends on accuracy of the color information of the TE image EP, and a score Sc(x, y) calculated based on the pixel value of which accuracy of the color information is low has low accuracy.

Generally, color of the color image is most vivid (i.e., has more color information) when the intensity is intermediate, while the saturation is lowered (i.e., the color information is lessened) when the intensity is lower or higher. That is, accuracy of the color information of the color image is influenced by the intensity. When the intensity is too high (typically, when halation is occurring) or when the intensity is too low, the saturation of the color image is extremely lowered, and accuracy of the color information of an object which is photographed as the color image is also lowered conspicuously. Further, accuracy of the color information is also lowered when the color channel (i.e., a color component) is saturated (i.e., a value of a color component has the maximum or substantially maximum value).

Incidentally, in the specification, a term "color channel" stands for each color component of pixel value of the color image (e.g., R(x, y), G(x, y) and B(x, y) of an RGB color image) or a grayscale image composed by one of the color components.

Since the score Sc(x, y) of which accuracy (reliability) is low could obstacle to the diagnosis, it is preferable that such a score Sc(x, y) will not be presented to a user (e.g., medical practitioners), or presented to the user together with reliability information thereof.

In the reliability evaluating process S8 according to the present embodiment, the reliability of the score Sc(x, y) of each pixel is evaluated based on the decision image data J{H(x, y), S(x, y), I(x, y)} used for calculating the score Sc(x, y) and the TE image data E{R'(x, y), G'(x, y), B'(x, y)} (i.e., quality decision of photographing condition is done based on the color balance of the endoscopic image).

Figure 11:
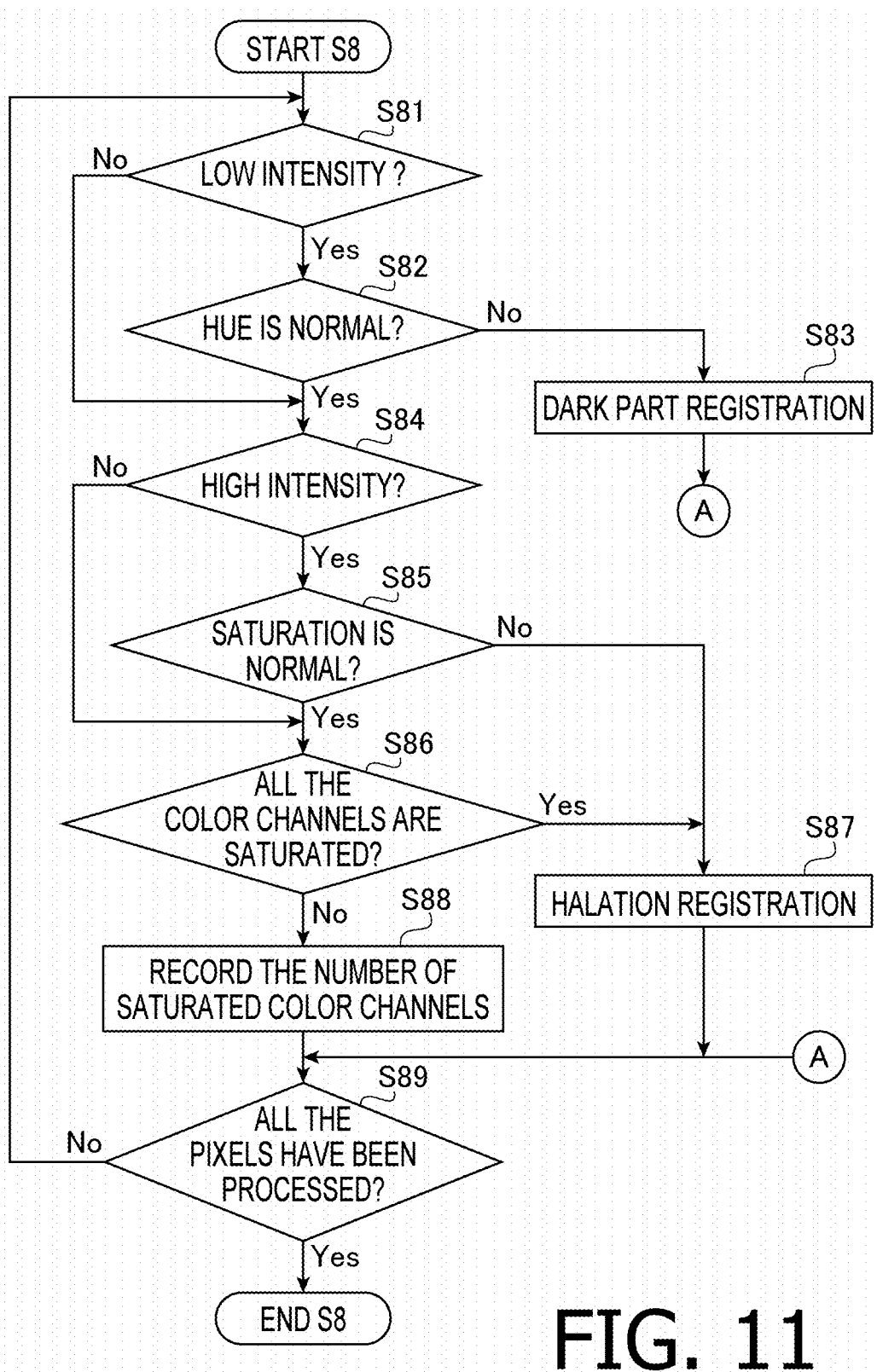
FIG. 11 is a flowchart illustrating a procedure of a reliability evaluating process.

FIG. 11 is a flowchart illustrating procedure of the reliability evaluating process S8. The reliability evaluating process S8 is executed sequentially for all the pixels (x, y).

[Low Intensity Judgment: S81]

In the reliability evaluating process S8, initially, a lower intensity judging process S81 to judge whether intensity is low or not is executed. Specifically, it is judged whether a value of the intensity I(x, y) is lower than a predetermined low intensity reference value (e.g., 0.3) or not. When the value of the intensity I(x, y) is lower than the low intensity reference value (S81: YES), there is a possibility that it is the dark part where the accuracy of the color information is extremely low, and a hue judging process S82 is executed subsequently. When the value of the intensity I(x, y) is equal to or greater than the lower intensity reference value (S81: NO), a high intensity judging process S84 is executed.

[Hue Judging: S82; Dark Part Registration: S83]

In the hue judging process S82, it is judged whether the value of hue H(x, y) is within a predetermined normal range (e.g., 60°-270°). This normal range corresponds to reddish color which is a distribution range of hue of a normal endoscopic image. When the value of hue H(x, y) is not within the normal range (i.e., when the color is out of a reddish color), it is considered that the accuracy of the hue H(x, y) is conspicuously low due to low intensity. Therefore, when the value of the hue H(x, y) is less than 60° or greater than 270° (S82: NO), the pixel (x, y) is determined to be a pixel in the "dark part" and an dark part registration, in which a judgment result of "dark part" is registered with the reliability information table CT, is executed (S83).

When the value of the hue H(x, y) is within the normal range of 60° or more and 270° or less (S82: YES), the high intensity judging process S84 is executed subsequently.

As above, through the low intensity judging process S81 and the hue judging process S82, whether the pixel (x, y) is of the "dark part" or not is judged.

[High Intensity Judgment: S84]

In high intensity judging process S84, whether a pixel is of a high intensity or not is judged. Specifically, it is judged whether a value of the intensity I(x, y) exceeds a predetermined high intensity reference value (e.g., 0.8) or not. When the value of the intensity I(x, y) exceeds the high intensity reference value (S84: YES), since there is a possibility that it is a halation part where the accuracy of the color information is extremely low, a saturation judging process S85 is executed subsequently. When the value of the intensity I(x, y) is equal to or less than the high intensity reference value (S84: NO), process S86 is executed subsequently.

[Saturation Judgment: S85; Halation Registration: S87]

In the saturation judging process S85, it is judged whether the value of saturation S(x, y) is within a predetermined normal range (e.g., 0.3-0.7) or not. This normal range is a distribution range of saturation of a normal endoscopic image. When the saturation S(x, y) is not within the normal range, it is considered that the accuracy of the saturation S(x, y) is conspicuously lowered due to the high intensity. Therefore, when the value of the saturation S(x, y) is less than 0.3 or greater than 0.7 (S85: YES), it is judged that the pixel (x, y) is a pixel of "halation" (i.e., a pixel in a part where the halation is occurring), and halation registration to register the result of judgment of "halation" with the reliability information table CT is executed (S87).

When the value of the saturation S(x, y) is equal to or greater than 0.3 and equal to or less than 0.7 (S85: YES), process S86 is executed subsequently.

[Color Channel Saturation Judgment: S86; Registration of Number of Saturated Color Channel: S88]

In process S86, the number of saturated color channels in the TE image data E is detected, and it is judged whether all the color channels are saturated. Specifically, it is judged whether each of the components R'(x, y), G'(x, y) and B'(x, y) of the TE image data E exceed a saturation reference value (e.g., 220) or not. When each of the components R'(x, y), G'(x, y) and B'(x, y) of the TE image data E exceeds the saturated reference value (S86: YES), the pixel (x, y) is judged to be the pixel of "halation," and the judgment result is registered with the reliability information table CT (S87).

When at least one of the components R'(x, y), G'(x, y) and B'(x, y) of the TE image data E is less than the saturation reference value (S86: NO), the number of saturated color channels is registered with the reliability information table CT (S88).

Until processing of all the pixels (x, y) has completed, above-described processes S81-S88 are repeated (S89).

[Marking: S9]

Next, based on the score Sc(x, y), marking process S9 to apply a mark indicating a location or a severity degree of a lesion part on the TE image data E (or, on the normal observation image NP) is executed.

Figure 12:
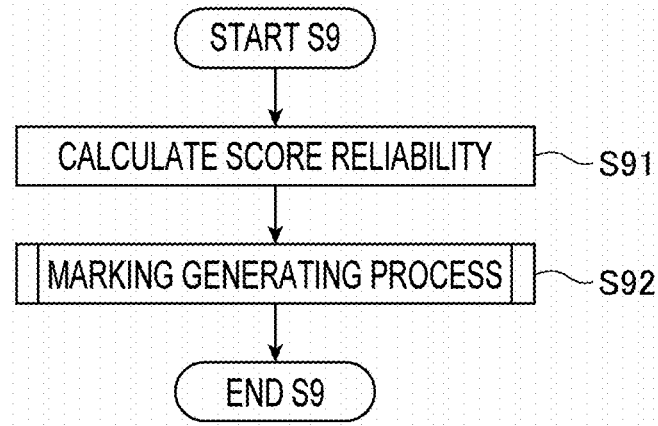
FIG. 12 is a flowchart illustrating a procedure of a marking process S9.

FIG. 12 is a flowchart showing procedure of marking process S9.

[Score Reliability Calculating: S91]

In the marking process S9, initially a score reliability calculating process S91 to calculate the score reliability SR is executed.

The score reliability calculation process S91 according to the present embodiment and described below is executed based on the TE image data E. However, the score reliability calculating process S91 may be configured to be executed based on the normal observation image data N. For example, when the score calculating process S7 is based on the decision image data J which is obtained by the color space converting process S5 of the normal observation image data N, the score reliability calculating process S91 is executed based on the normal observation image data N.

The score reliability SR is calculated using formula 9 as a rate of pixels (x, y) having the scores Sc(x, y) regarded to have certain reliability. That is, the score reliability SR is calculated as a rate of the number of pixels which are not subject to the dark part registration S83 or the halation registration S87 in the reliability evaluating process S8 to the number of all the pixels of the TE image EP.

$$SR = \frac{N_{EP} - (N_{dark} + N_{halation})}{N_{EP}} \quad \text{[Formula 9]}$$

where,
$N_{EP}$: the number of all the pixels of the TE image EP;
$N_{dark}$: the number of pixels of the TE image EP subject to the dark part registration S83; and
$N_{halation}$: the number of pixels of the TE image EP subject to the halation registration S87.

[Marking Image Generation: S92]

Following the score reliability calculating process S91, a marking image generating process S92 to generate a marking image MP S92 is executed.

Figure 13:
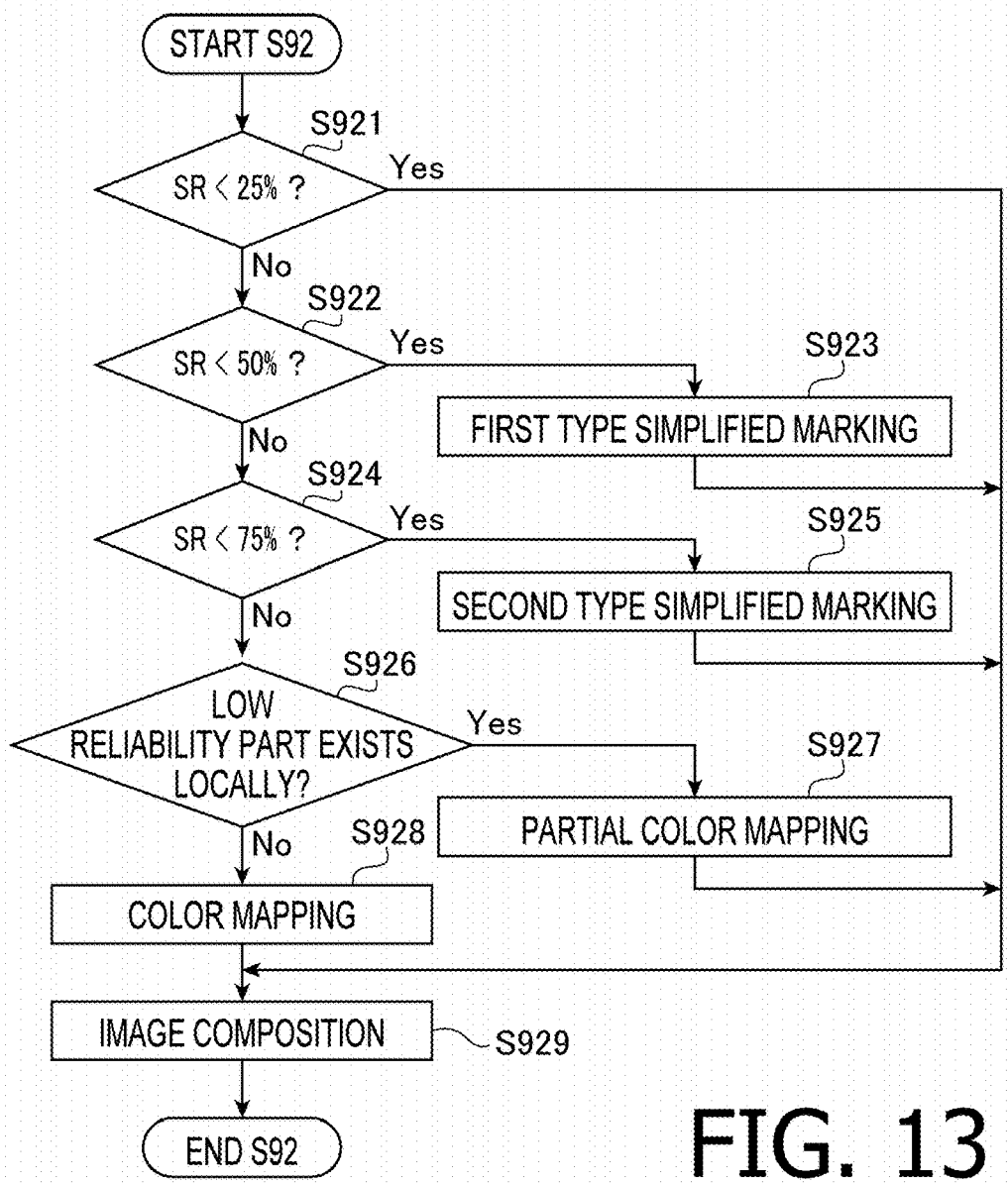
FIG. 13 is a flowchart illustrating a procedure of a marking image generating process.

FIG. 13 is a flowchart showing a procedure of the marking image generating process S92.

Figure 14:
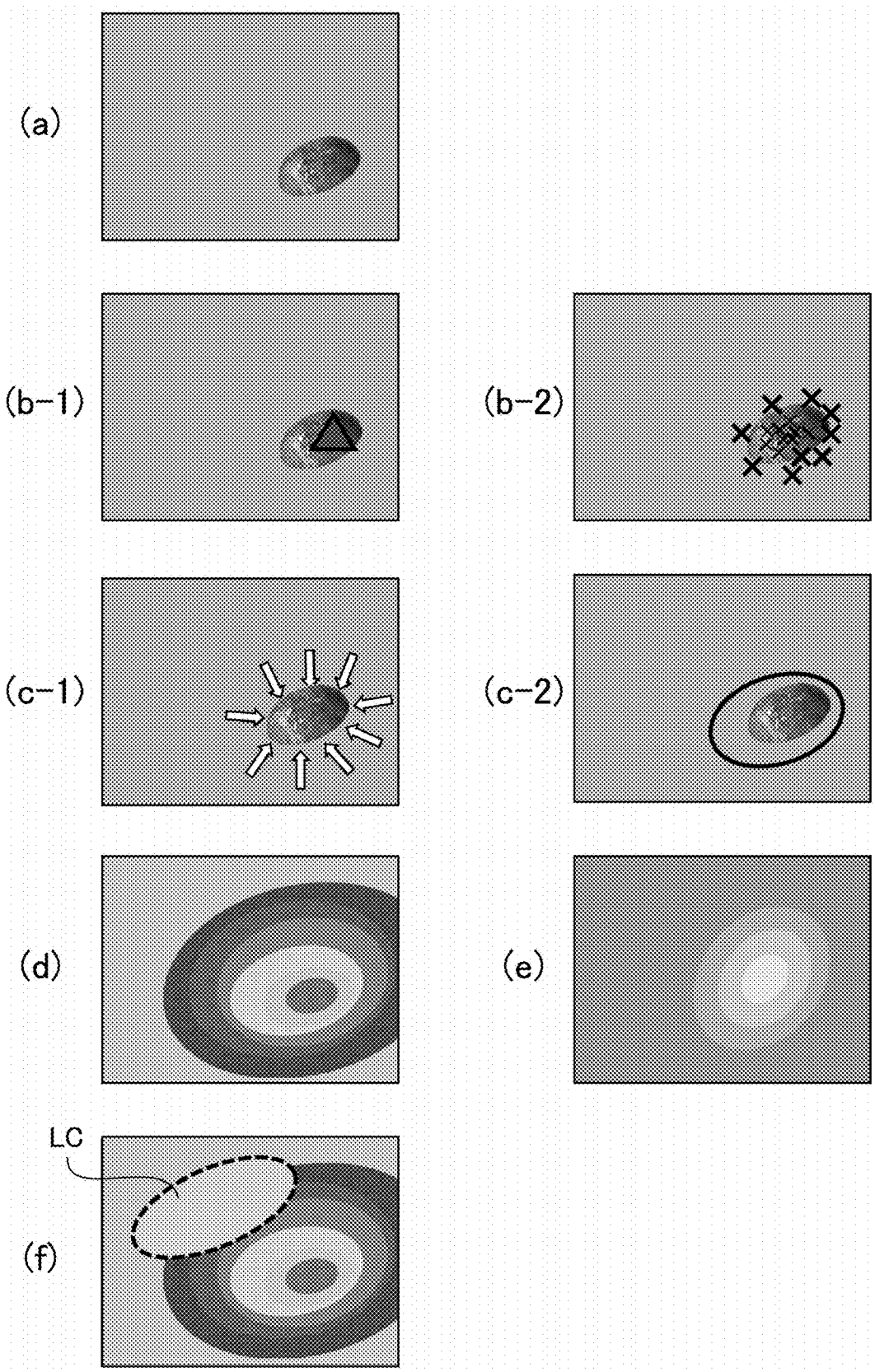
FIG. 14 shows composite images CP generated in the marking image generating process.

FIG. 14 shows a marking image MP (to be precise, a composite image CP in which a marking image MP is overlaid on and combined with a TE image EP) generated by the marking image generating process S92.

In the marking image generating process S92, five kinds of marking images MP are generated depending on the score reliability of the TE image EP (S921-S928). Further, a composite image CP, which is configured such that the generated marking image MP is overlaid and combined onto the TE image EP, is generated (S929).

Although, the marking image MP is overlaid and combined onto the TE image EP in the marking image generating process S92 according to the present embodiment, the marking image MP may be overlaid onto and combined with the normal observation image NP.

When almost all the pixels of the TE image EP are pixels (x, y) of which reliability of the scores SC(s, y) are extremely low (i.e., pixels which do not exhibit certain reliability) and the score reliability SR is very low (e.g., the score reliability SR is less than 25%) (S921: YES), a sufficiently practical marking image MP cannot be generated, and thus no marking images MP are generated.

In this case, in the image generating process S929, a null marking image MP is overlaid on the TE image EP and combined therewith. That is, as shown in FIG. 14(a), a TE image EP on which no marks are applied is stored in a storage area Pc as it is, as a composite image CP.

[First Type Simplified Marking Process: S923]

When the reliability is relatively low (e.g., when the score reliability SR is 25% or more, and less than 50%) (S922: YES), a first type simplified marking process S923, in which a marking image MP formed with a predetermined mark (e.g., a symbol "▲") applied on a pixel having the maximum score Sc as shown in FIG. 14(b-1) is generated and stored in a stored area Pm is executed. According to this configuration, the user can surely grasp a part the maximum severity degree (which is in the vicinity of the center of the lesion part in many cases).

In the first type simplified marking process S923, predetermined marks (characters, numbers or symbols) and figures are applied as marks. Further, the mark is applied such that a centroid of the mark coincides with the pixel having the maximum score Sc (or a centroid of an image area having the maximum score Sc). It is noted that the color or size of the mark may be changed in accordance with the value of the maximum score Sc. With such a configuration, the user can intuitively grasp the severity degree as well.

FIG. 14(b-2) shows a modified example of the marking image MP generated by the first type simplified marking process S923. In this modified example, multiple predetermined marks (symbol "X") of which sizes correspond to the scores Sc(x, y) are applied on the pixels (x, y) of which scores Sc(x, y) are equal to or greater than a predetermined threshold value. Further, the multiple marks are applied not to overlap with each other so that each mark can be discriminated. According to this configuration, positions and distribution (shape) of areas with high severity degree can be grasped easily.

[Second Type Simplified Marking Process: S925]

When the reliability is relatively high (e.g., when the score reliability SR is 50% or more, and less than 75%) (S924: YES), a second type simplified marking process S925 to generate a marking image MP applied with marks which appear to encircle an area in which the score Sc(x, y) is high, as shown in FIGS. 14(c-1) and (c-2). It is noted that FIG. 14(c-1) is an example in which the marks including multiple sings and figures (e.g., an arrow) are arranged to encircle the area where the scores Sc(x, y) are high, and FIG. 14(c-2) is an example in which a ring-like mark encircling the area where the scores S(x, y) are high is applied.

[Color Mapping Process: S928]

When the reliability is very high (e.g., when the score reliability SR is 75% or more) (A924: NO), and pixels (x, y) of which scores Sc(x, y) have extremely low do not locally exist (S926: NO), a color mapping process S928 (entire color mapping process) is executed. In the color mapping process S928, a color map image in which pixels of lesion part are colored with colors corresponding to the scores Sc(x, y) is generated as a marking image MP.

In the color mapping process S928, firstly, a display color table DCT stored in the memory 229 is referred to and display color Col(x, y) to be applied to each pixel (x, y) is determined based on the score Sc(x, y). Next, color map image data M (i.e., a marking image MP) having the display colors Col(x, y) as pixel values is generated, and stored in the storage area Pm of the image memory 227.

Incidentally, the display color table DCT is a numerical table defining correspondence between the scores Sc(x, y) and color codes defining display colors Col(x, y) of the color map image. An example of the display color table DCT is shown in Table 1. As the display colors, different colors are set for eleven steps of scores Sc(x, y), respectively. It is noted that, to the pixels (x, y) of which scores Sc(x, y) are zero (i.e., normal tissues), a null value indicating colorless and transparent is given. Therefore, pixels corresponding to the normal tissues are not colored in the color mapping process S928. Further, designation of a color to be applied to each pixel (x, y) need not be limited to designation using RGB, but designation with any other expression of colors (e.g., hue and/or saturation) may be used.

TABLE 1

| Score Sc | | 0.0 | 0.1 | 0.2 | 0.3 | 0.4 | 0.5 | 0.6 | 0.7 | 0.8 | 0.9 | 1.0 |
|---|---|---|---|---|---|---|---|---|---|---|---|---|
| DISPLAY | R value | null | 0 | 0 | 0 | 0 | 0 | 0 | 255 | 255 | 255 | 128 |
| COLOR | G value | null | 0 | 0 | 128 | 128 | 255 | 255 | 255 | 0 | 0 | 128 |
| Col | B value | null | 255 | 128 | 128 | 0 | 0 | 255 | 0 | 0 | 255 | 0 |

FIG. 14(e) shows a modification of the color map image. This modification shows a grayscale color map image composed of achromatic colors only having intensity information. For example, when the score reliability SR is low, the color map according to the modification may be displayed instead of the marking maps MP shown in FIGS. 14(a)-(c-2). By using achromatic colors, the user can grasp intuitively that the score reliability SR is low, and obtain detailed information regarding the severity degree.

In the color mapping process S928, for example, two types of display color tables DCTs (i.e., a chromatic color table and achromatic color table) depending on presence/absence of the reliability of the scores. Sc(x, y), and color mapping with use of chromatic colors may be executed with respect to the pixels (x, y) of which the scores Sc(x, y) have certain reliability, while color mapping with use of achromatic colors may be executed with respect to the pixels (x, y) of which scores Sc(x, y) do not have certain reliability.

[Partial Color Mapping Process: S927]

When the score reliability SR is very high (S924: NO) and pixels (x, y) of which scores Sc(x, y) have extremely low reliability exist locally (S926: YES), a partial color mapping process S927 to apply color mapping with respect to an area excluding an area LC, in which the pixels (x, y) of which scores Sc(x, y) are extremely low exist locally, is executed. It is noted that, although pixels (x, y) of which scores Sc(x, y) having high reliability are included in area LC, the number of such pixels is small and a useful mapping image is not formed. In the partial color mapping process S928, by excluding the area LC in a lump, including the pixels (x, y) of which scores Sc(x, y) having high reliability, from targets for the color mapping, calculation amount necessary for the color mapping cane be reduced largely. Further, since the area LC is excluded, in a lump, from the target of the color mapping, the user can easily gasp the area LC where the reliability of the scores Sc(x, y) are low.

[Display Screen Generation: S10]

When the marking process S9 has completed, a display screen generating process S10 is executed subsequently. The display screen generating process S10 is a process to generate display screen data to be displayed on the monitor 900 with use of various pieces of image data stored in the image memory 227, and executed by the display screen generating part 228 of the image processing circuit 220. The display screen generating part 228 is configured to generate multiple types of display screen data under control of the system controller 202.

Figure 15:
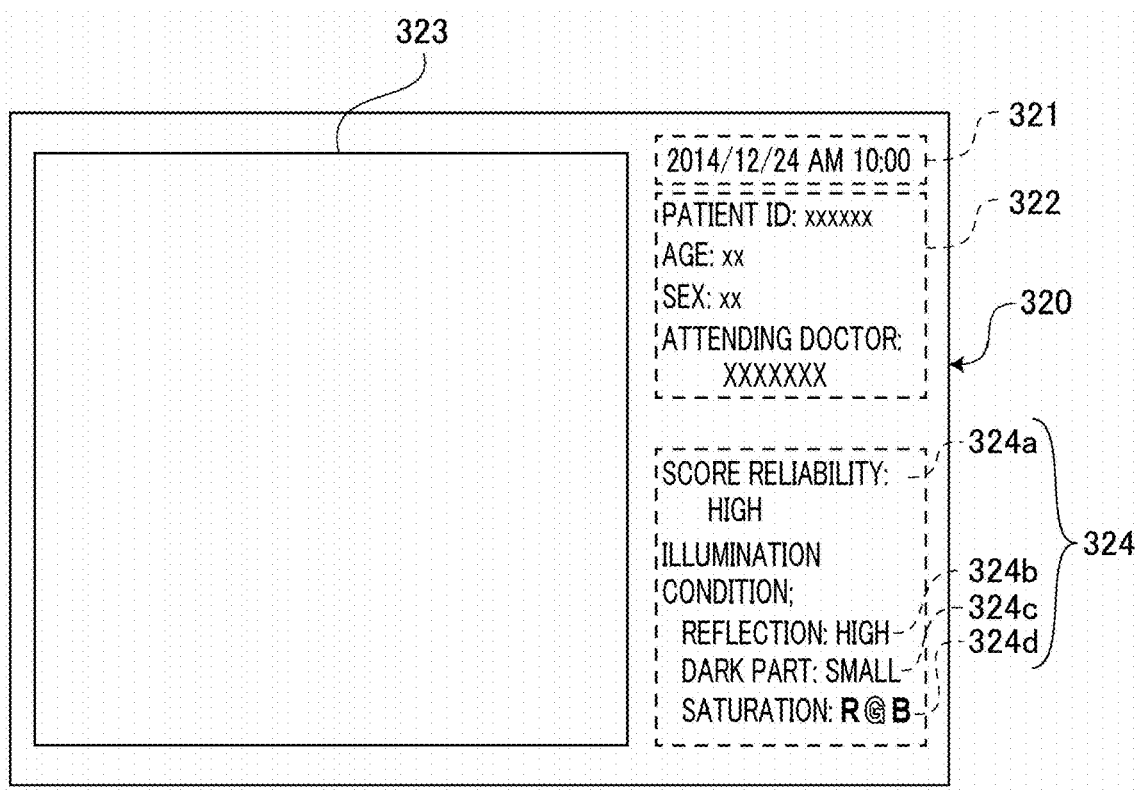
FIG. 15 is an analysis mode observation screen generated in a display screen generating process.

FIG. 15 is an example of the display screen generated in the display screen generating process S10, and shows an analysis mode observation screen 320 displayed during endoscopic observation in the image analysis mode. The analysis mode observation screen 320 has a date/time displaying area 321 to display photographing date and time are displayed, a basic information displaying area 322 to display basic information related to inspection (e.g., an identification number, age and sex of a patient, a name of a doctor in charge), a image display area 323 to display the marking image MP and/or the TE image EP (or the normal observation image NP), and an analysis accuracy information displaying area 324 to display information related to analysis accuracy (i.e. evaluation result in the reliability evaluating process S8).

In the analysis accuracy information displaying area 324, a display 324a of the score reliability SR, a display (i.e., a dark part rate display) 324b of a rate of pixels (x, y) subject to the dark part registration S83, a display a reflection part rate display) 324c of a rate of pixels (x, y) subject to the halation registration S87, and a display (i.e., a saturated channel display) 324d of the saturated color channel are included.

The display 324a of the score reliability SR is displayed with "HIGH," "MEDIUM" and "LOW" depending on the value of the score reliability SR. For example, "HIGH" is displayed when the score reliability SR is 75% or more, "MEDIUM" is displayed on the score reliability is 25% or more, and less than 75%; and "LOW" is displayed when the score reliability SR is less than 25%.

It is noted that the color (one or more of hue, saturation and intensity) and/or the size of the display 324a of the score reliability SR may be varied depending on the value of the score reliability SR. Further, the score reliability SR may be displayed discriminatingly by a background color of the analysis mode observation screen 320 (or the analysis accuracy information displaying area 324).

The dark part rate display 324b is displayed with three steps of "MANY," "MEDIUM" and "SMALL" depending on the rate of the number $N_{dark}$ of pixels subjected to the dark part registration S83 with respect to the number $N_{EP}$ of all the pixels of the TE image EP. For example, when the number $N_{dark}$ of the pixels subjected to the dark part registration S83 is 50% or more, "MANY" is displayed, when t0% or more, and less than 50%, "MEDIUM" is displayed, and when less than 10%, "SMALL" is displayed.

Similarly to the dark rate part display 324b, the reflection part rate display 324c is displayed with three steps of "MANY," "MEDIUM" and "SMALL" depending on the rate of the number $N_{halation}$ of the pixels subjected to the halation registration S87 with respect to all the number $N_{EP}$ of the TE image EP. For example, when the number $N_{halation}$ of the pixels subjected to the halation registration S87 with respect to the number $N_{EP}$ of all the pixels of the TE image EP is 50% or more, "MANY" is displayed, when 10% or more, and less than 50%, "MEDIUM" is displayed, and "SMALL" is displayed when less than 10%.

It is noted that the color (one of more of hue, saturation and intensity) of the dark rate display 324b (or the reflection part rate display 324c) may be changed in accordance with the rate of the pixels subjected to the dart part registration S83 (or the halation registration S87).

The saturated channel display 324d is displayed with a saturated color channel (e.g., a color channel in which saturation is occurring in more than a predetermined number pixels). For example, a symbol (e.g., a character "R," "G" or "B") or a figure indicating the saturated color channel is displayed with the same hue of the color channel (for example, in red for R channel) at high saturation and high intensity: Further, a symbol (e.g., a character "B") indicating the non-saturated color channel (e.g., the B channel) may not be displayed, or may be displayed inconspicuously in achromatic color (e.g., gray) at low intensity. When the saturated (or, non-saturated) color channel may be displayed simply by color without using symbols or the like.

In the display screen generating process S12, the display screen generating part 228 retrieves the marking image data M from storage area group Pm in the image memory 227, and/or retrieves the TE image data E from the storage area group Pe (or retrieves the normal observation image data N from the storage area group Pn), and displays the same on the image display area 323. Further, in the date display area 312 and basic information display area 322, information supplied by the system controller 202 is displayed.

[Output Processing: S11]

To the display screen data generated in the display screen generating process S10, processes like a gamma compensation are applied and is output to the monitor 900 (output processing S11) by the output circuit 220b.

The operator performs an endoscopic observation with watching the analysis mode observation screen 320. Specifically, the operator performs the endoscopic observation with watching the marking image MP displayed in the image display area 323. By observing the marking portions on the marking image MP particularly carefully, accurate medical examination can be possible without overlooking lesion parts.

After completion of the display screen generating process S10 and the outputting process S11, it is judged whether the endoscopic observation is to be continued (S12). Until a user operation on the operation panel 214 of the processor 200 to instruct the end of the endoscopic observation or stop driving the electronic endoscope apparatus 1 (S12: NO), the above processes S1-S11 are repeated.

Second Embodiment

Next, a second embodiment of the present invention will be explained.

Figure 16:
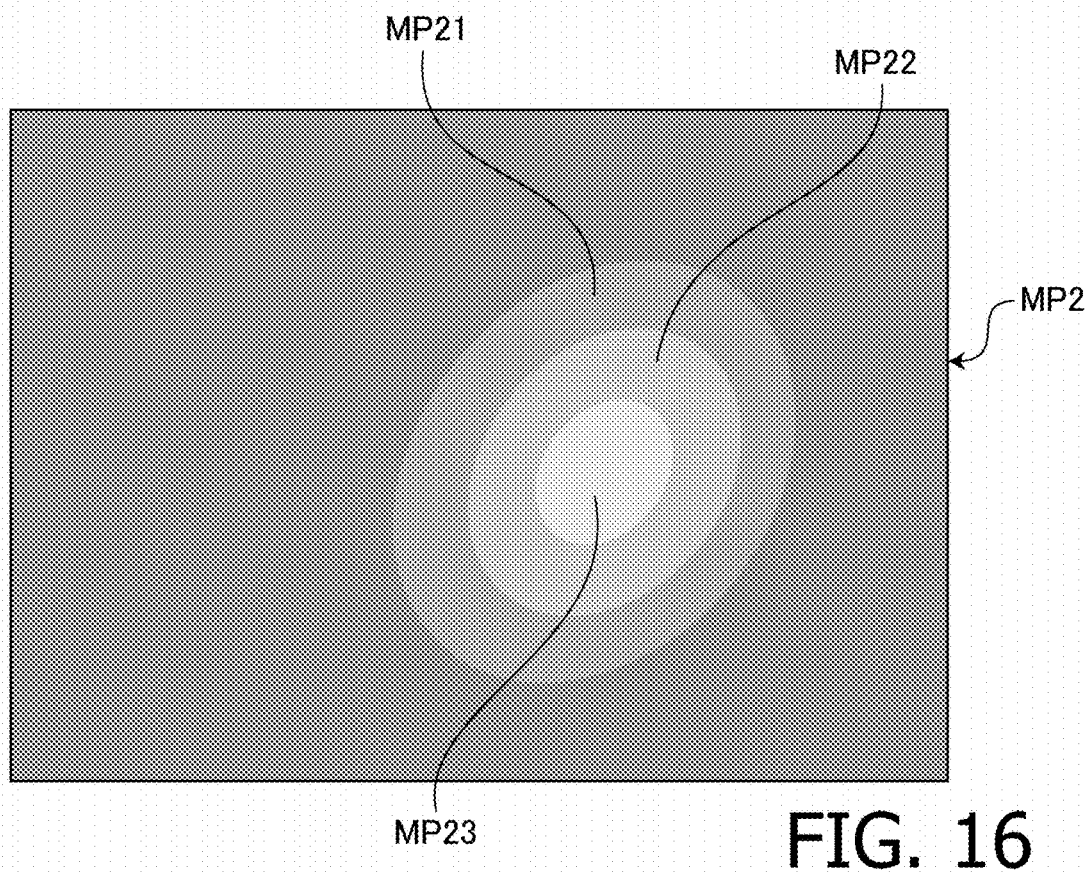
FIG. 16 shows a marking image MP2 (i.e., a color map image) according to a second embodiment.

FIG. 16 is a marking image MP2 (i.e., a color map image) according to the second embodiment.

In the color mapping procedure according to the present embodiment, the reliability information table CT is referred to, and coloring based on the display color table DCT shown in Table 1 is not applied to the pixels in which saturation of the color channel is occurring, but the pixels are colored with achromatic colors having intensity information corresponding to the number of saturated color channels (i.e., grayscale). According to the present embodiment, the more the number of saturated color channels is, the higher the given intensity is. In the marking image MP2 shown in FIG. 16, an area MP21 is an area in which the saturation is occurring in one color channel, an are MP22 is an area in which the saturation is occurring in two color channels, and an area MP23 is an area in which the saturation is occurring in three color channels.

To the pixels in which the saturation of the color channels are not occurring and which are not subjected to the dark part registration S83 or the halation registration S87, the color mapping is applied, based on Table 1, corresponding to the severity degree. Since the color map indicating the severity degree uses the colors from one having the higher saturation, even if it is mixed with an achromatic color map indicating the degree of saturated color channels, one can discriminate one from the other easily.

The pixels subjected to the halation registration S87 may be colored with the same color used for the area MP23 (or, achromatic color brighter than that of the area MP23). Further, the pixels subjected to the dark part registration S83 may be colored with achromatic color which is darker than the area MP21.

It is noted that the above embodiments are examples where the present invention is applied to the electronic endoscope systems. However, the present invention needs not be limited to such a configuration. For example, the present invention can be applied to an image reproducing device configured to reproduce endoscopic observation images photographed by the electronic endoscope apparatus. The present invention can also be applied to an observation image other than the endoscopic images (e.g., observation images taken with ordinary video cameras, or observation images inside a human body during operations).

The foregoing is the description of the illustrative embodiments. Embodiments of the present invention are not limited to those described above, and various modifications can be made within technical philosophy of the present invention. For example, appropriate combinations of illustratively indicated embodiments in the specification are also included in embodiments of the present invention.

What is claimed is:

1. An image processing apparatus, comprising:
    an imager configured to obtain image data acquired by photographing biological tissue;
    a processor; and
    a memory storing instructions that, when executed by the processor, cause the processor to perform operations including:
        converting pixel values of the image data into pixel values of a predetermined color space;
        determining whether a pixel is a pixel photographing an inflammation part, for each pixel, based on a saturation value and a hue value included in the converted pixel value;
        calculating, for each pixel, a hue correlation value between a hue value of blood and the hue value of the converted pixel value, and a saturation correlation value between a saturation value of blood and the saturation value of the converted pixel value;
        calculating a score representing a degree of severity of inflammation of the biological tissue photographed in an image represented by the image data for each pixel determined as the pixel photographing an inflammation part, based on the calculated saturation correlation value and the calculated hue correlation value included in the converted pixel value;
        evaluating a reliability of the score for each said pixel determined as the pixel photographing an inflammation part, based on the saturation correlation value or the hue correlation value included in the converted pixel value; and
        calculating a score reliability which represents a ratio of pixels of which scores having predetermined reliability to all the pixels of the image data.

2. The image processing apparatus according to claim 1, wherein the evaluating includes determining whether each pixel is in a halation state based on a pixel value, and
    wherein the evaluating includes excluding pixels determined to be in the halation state from the pixels of which scores having the predetermined reliability.

3. The image processing apparatus according to claim 1, wherein the evaluating includes determining whether a pixel is of a dark part based on a pixel value thereof, and
    wherein the evaluating includes excluding pixels determined to be of the dark part from the pixels of which scores having the predetermined reliability.

4. The image processing apparatus according to claim 1, wherein the operations further include converting the pixel values of the image data into pixel values of a hue-saturation-intensity space, and
    wherein the evaluating includes evaluating the reliability of the scores based on intensity of each pixel output by the converting.

5. The image processing apparatus according to claim 1, wherein the evaluating includes determining whether each pixel is a saturated pixel of which any one of color channels is saturated based on a pixel value thereof, and
    wherein the evaluating includes excluding pixels determined to be the saturated pixels from the pixels of which scores having the predetermined reliability.

6. The image processing apparatus according to claim 5, wherein the determining whether each pixel is a saturated pixel of which any one of color channels is saturated includes counting the number of saturated color channels based on the pixel values, and
    wherein the determining whether each pixel is a saturated pixel of which any one of color channels is saturated includes determining the pixels having a predetermined number or more of saturated color channels as the saturated pixel.

7. The image processing apparatus according to claim 1, wherein the operations further include applying marks indicating a distribution of the scores on the image, and
    wherein the applying includes changing modes of the marks depending on the score reliability.

8. The image processing apparatus according to claim 7, wherein the applying includes executing a first color mapping to change pixel colors of a lesion part to a color corresponding to the score.

9. The image processing apparatus according to claim 8, wherein the applying includes excluding the image area in which pixels of which reliabilities are low are locally existing.

10. The image processing apparatus according to claim 8, wherein the applying includes applying the first color mapping with use of different colors for pixels of which scores have the predetermined reliability and pixels of which scored do not have the predetermined reliability.

11. The image processing apparatus according to claim 7, wherein the applying includes applying a first type simplified marking process in which a mark is applied on an area, of which score is equal to or greater than a predetermined value, in the image.

12. The image processing apparatus according to claim 7, wherein the applying includes applying a second type simplified marking process in which a mark is applied such that the mark encircles an area of which score is relatively high in the image.

13. The image processing apparatus according to claim 1, wherein the operations further include displaying an evaluation result of the reliability of the score.

14. The image processing apparatus according to claim 1, wherein quality of a photographing condition is determined in accordance with a color balance of the image.

15. The image processing apparatus according to claim 1,
wherein the image is photographed with use of a single-broadband illumination light.

16. The image processing apparatus according to claim 2,
wherein the evaluating includes determining whether a pixel is of a dark part based on a pixel value thereof, and
wherein the evaluating includes excluding pixels determined to be of the dark part from the pixels of which scores having the predetermined reliability.

17. The image processing apparatus according to claim 16,
wherein the operations further include converting the pixel values of the image data into pixel values of a hue-saturation-intensity space,
wherein the evaluating includes evaluating the reliability of the scores based on intensity of each pixel output by the converting.

18. The image processing apparatus according to claim 17,
wherein the evaluating comprises determining whether each pixel is a saturated pixel of which any one of color channels is saturated based on a pixel value thereof, and
wherein the evaluating includes excluding pixels determined to be the saturated pixels from the pixels of which scores having the predetermined reliability.

19. The image processing apparatus according to claim 18,
wherein the determining whether each pixel is a saturated pixel comprises counting the number of saturated color channels based on the pixel values, and
wherein the determining whether each pixel is a saturated pixel comprises determining the pixels each having a predetermined or more number of saturated color channels as the saturated pixel.

20. The image processing apparatus according to claim 19,
wherein the operations further include applying marks indicating a distribution of the scores on the image, and
wherein the applying includes changing modes of the marks depending on the score reliability.

* * * * *